(12) United States Patent
Manemann et al.

(10) Patent No.: US 7,766,653 B2
(45) Date of Patent: Aug. 3, 2010

(54) METHOD AND APPARATUS FOR SELECTING A PRESCRIPTION FOR AN ORTHODONTIC BRACE

(75) Inventors: Robert C. Manemann, Corona, CA (US); Russell A. Jordan, Rancho Cucamonga, CA (US)

(73) Assignee: 3M Innovative Properties Co, St. Paul, MN (US)

( * ) Notice: Subject to any disclaimer, the term of this patent is extended or adjusted under 35 U.S.C. 154(b) by 660 days.

(21) Appl. No.: 11/555,415

(22) Filed: Nov. 1, 2006

(65) Prior Publication Data

US 2007/0054231 A1 Mar. 8, 2007

Related U.S. Application Data

(63) Continuation of application No. 09/918,226, filed on Jul. 30, 2001, now Pat. No. 6,733,289, and a continuation of application No. 10/841,156, filed on May 7, 2004, now abandoned.

(51) Int. Cl.
*A61C 3/00* (2006.01)
(52) U.S. Cl. ............................................. 433/24; 705/3
(58) Field of Classification Search ................... 433/24; 705/3
See application file for complete search history.

(56) References Cited

U.S. PATENT DOCUMENTS

| | | | |
|---|---|---|---|
| 5,011,405 A | 4/1991 | Lemchen | |
| 5,027,281 A | 6/1991 | Rekow et al. | |
| 5,055,039 A | 10/1991 | Abbatte et al. | |
| 5,139,419 A | 8/1992 | Andreiko et al. | |
| 5,273,429 A | 12/1993 | Rekow et al. | |
| 5,395,238 A | 3/1995 | Andreiko et al. | |
| 5,798,924 A | 8/1998 | Eufinger et al. | |
| 5,851,115 A | 12/1998 | Carlsson et al. | |
| 5,879,158 A | 3/1999 | Doyle et al. | |
| 5,882,192 A | 3/1999 | Bergersen | |
| 5,975,893 A | 11/1999 | Chishti et al. | |
| 6,049,743 A | 4/2000 | Baba | |
| 6,068,482 A | 5/2000 | Snow | |
| 6,089,868 A | 7/2000 | Jordan et al. | |
| 6,152,731 A | 11/2000 | Jordan et al. | |
| 6,227,850 B1 | 5/2001 | Chishti et al. | |

(Continued)

FOREIGN PATENT DOCUMENTS

EP 0 502 227 9/1992

(Continued)

*Primary Examiner*—Cris L Rodriguez
*Assistant Examiner*—Eric Rosen
(74) *Attorney, Agent, or Firm*—Kevin W. Weber

(57) ABSTRACT

A prescription for an orthodontic brace is selected by providing data representing a number of teeth of the dental arch and by displaying images of the teeth in two or more different positions. Images of at least one tooth when in the first position and when in the second position are simultaneously displayed in superimposed fashion, and any difference in orientations of the displayed tooth images between the first position and the second position appears in contrast. As a consequence, the relative difference in positions can be readily observed. The invention is particularly useful for selecting a prescription of a brace from two or more prescriptions, and is also useful for observing the relative effect of a single prescription when used on certain teeth in comparison to the position of the same teeth during an earlier stage of treatment.

13 Claims, 15 Drawing Sheets

U.S. PATENT DOCUMENTS

| | | |
|---|---|---|
| 6,244,861 B1 | 6/2001 | Andreiko et al. |
| 6,250,918 B1 | 6/2001 | Sachdeva et al. |
| 6,309,215 B1 | 10/2001 | Phan et al. |
| 6,318,994 B1 | 11/2001 | Chishti et al. |
| 6,464,496 B1 | 10/2002 | Sachdeva et al. |
| 6,733,289 B2 | 5/2004 | Manemann et al. |
| 6,739,869 B1 * | 5/2004 | Taub et al. .................. 433/24 |
| 2002/0010568 A1 | 1/2002 | Rubbert et al. |
| 2002/0025503 A1 | 2/2002 | Chapoulaud et al. |
| 2006/0064329 A1 | 3/2006 | Abolfathi et al. |

FOREIGN PATENT DOCUMENTS

| | | |
|---|---|---|
| WO | WO 91/11959 | 8/1991 |
| WO | WO 97/03622 | 2/1997 |
| WO | WO 99/34747 | 7/1999 |
| WO | WO 00/19935 | 4/2000 |
| WO | WO 01/47405 | 7/2001 |

* cited by examiner

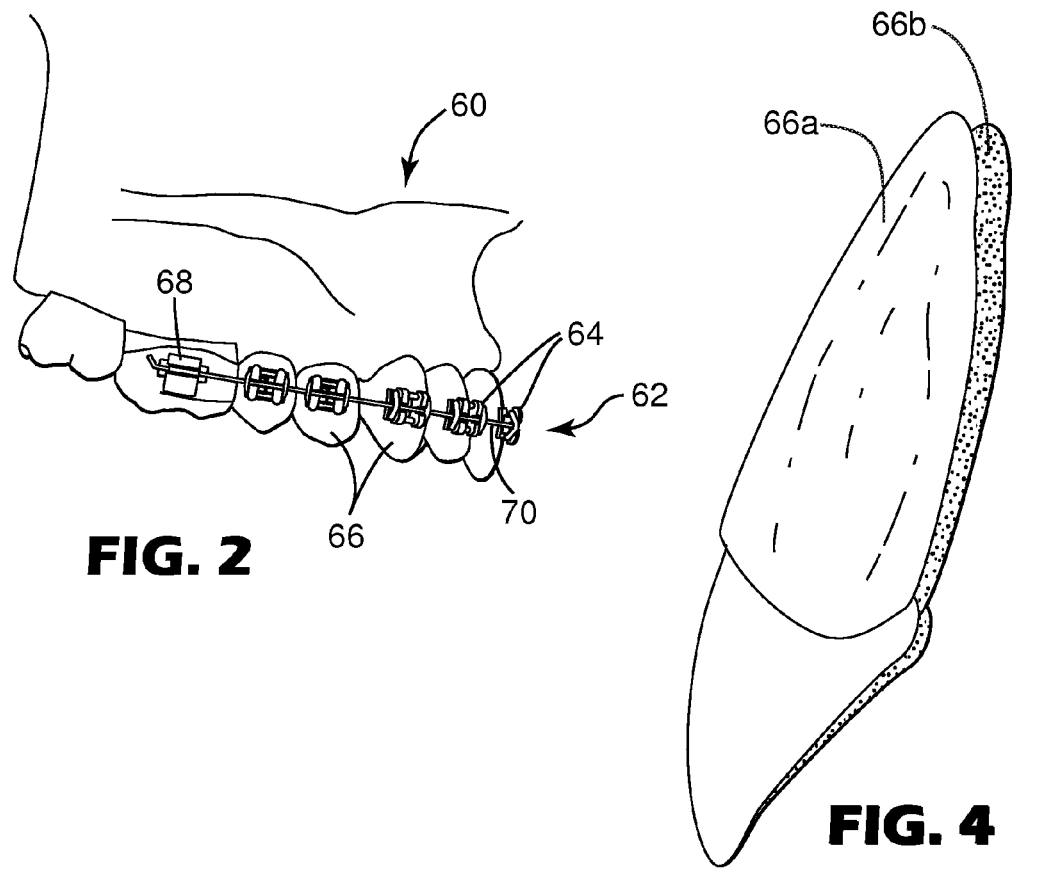
FIG. 2
FIG. 4
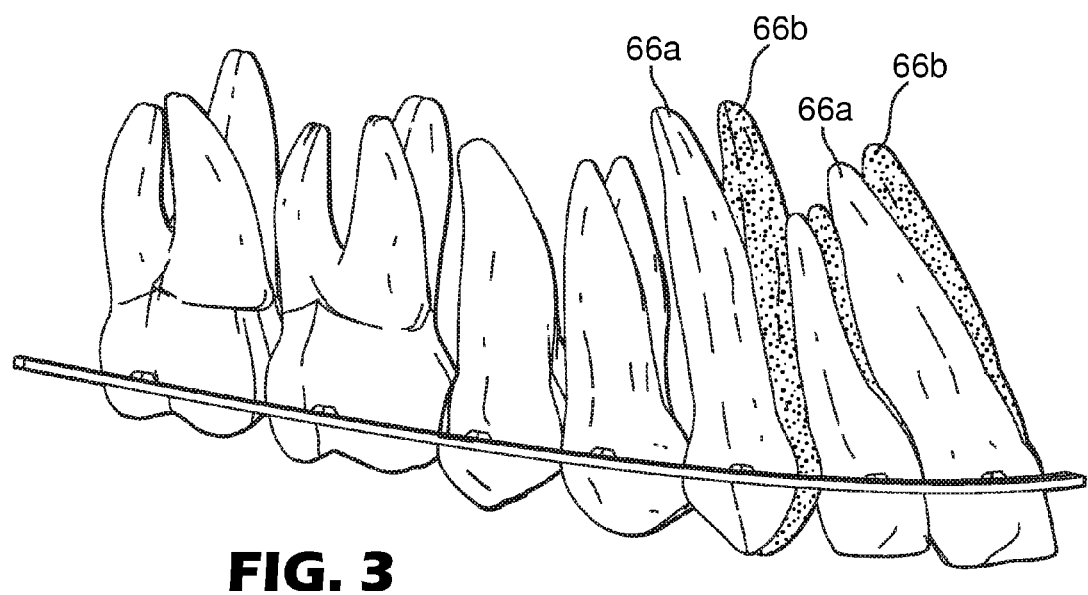
FIG. 3

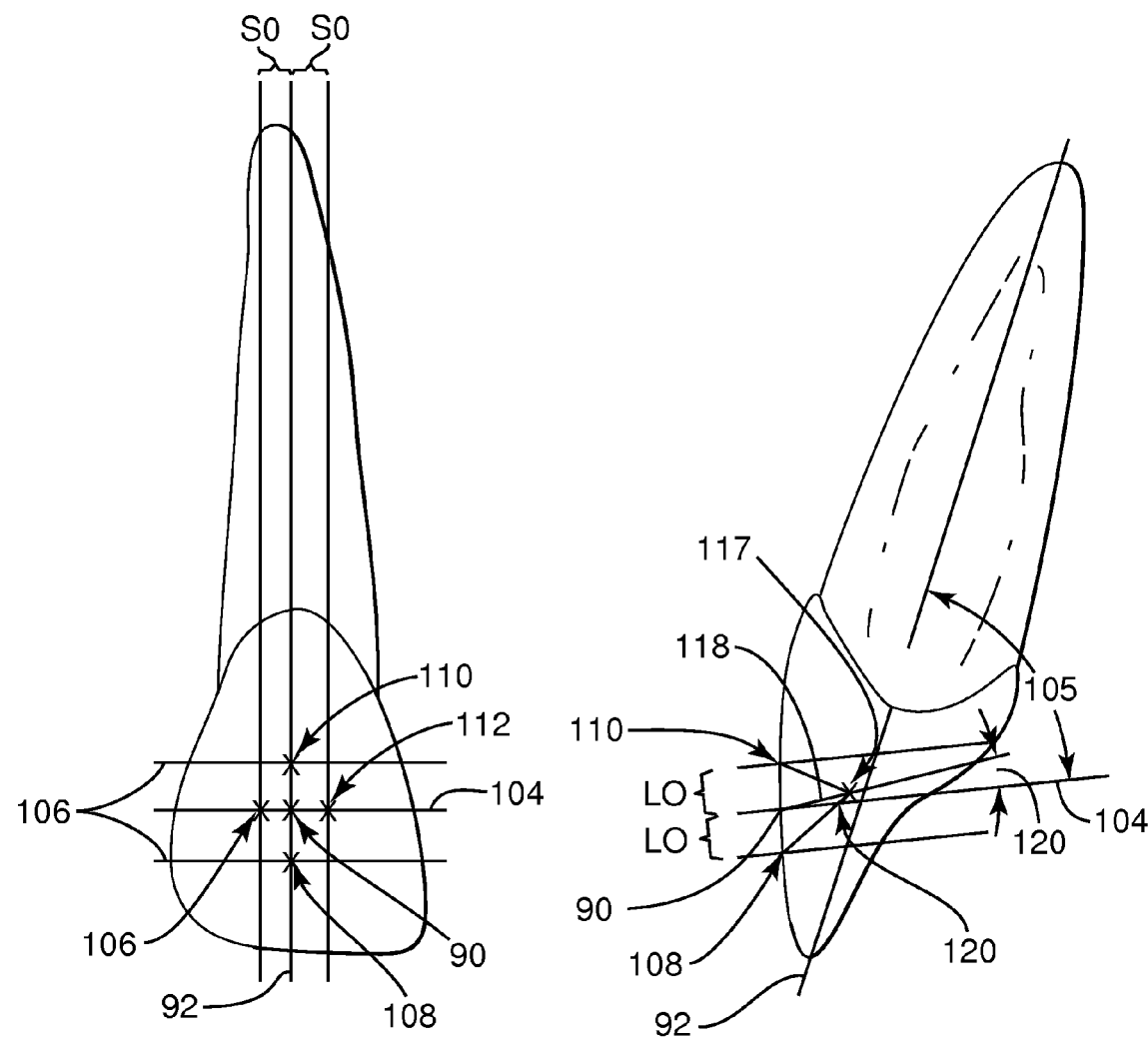
FIG. 8   FIG. 9
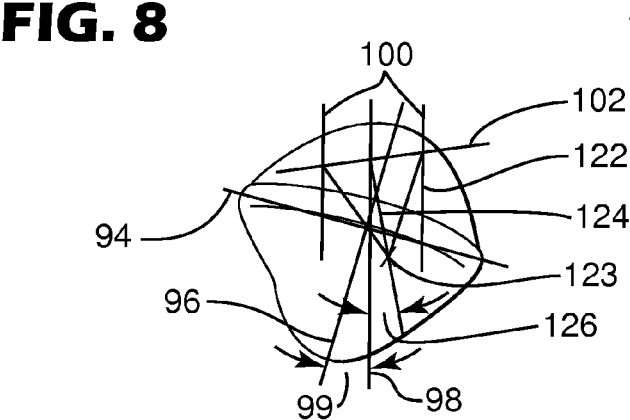
FIG. 10

METHOD AND APPARATUS FOR SELECTING A PRESCRIPTION FOR AN ORTHODONTIC BRACE

CROSS REFERENCE TO RELATED APPLICATIONS

This application is a continuation of U.S. Ser. No. 09/918,226, filed Jul. 30, 2001, now issued as U.S. Pat. No. 6,733,289 and U.S. Ser. No. 10/841,156 filed, May 7, 2004, currently pending.

BACKGROUND OF THE INVENTION

1. Field of the Invention

This invention relates to methods and apparatus used in the treatment of an orthodontic patient. More particularly, the present invention is directed to methods and apparatus for selecting an orthodontic brace made of one or more components that have been chosen to facilitate achieving a particular objective as determined by the practitioner.

2. Description of the Related Art

Orthodontia is a branch of dentistry that prevents or treats irregular positions of the teeth. Teeth that are not in correct positions may hinder proper chewing of food, and may also tend to develop caries or contribute to gum disease. Furthermore, malpositioned teeth may present an unsightly appearance, especially if located in front or anterior portions of the patient's oral cavity.

An orthodontic brace is a device used to move teeth to orthodontically correct positions along the dental arch. Typically, the orthodontic practitioner will create a custom orthodontic brace for each patient by selecting components that apply gentle pressure to the teeth in certain directions. Over a period of time, the teeth tend to slowly shift toward desired positions. After an extended period of time, the growth of new bone tissue in areas next to the roots of the teeth will firmly hold the teeth in their new positions.

One type of orthodontic brace that is in widespread use comprises a set of orthodontic appliances along with an archwire. The appliances typically include a number of small, slotted brackets, each of which is mounted on a corresponding tooth along the dental arch. An archwire is received in the slot of each bracket and forms a track to guide the teeth toward desired positions. Usually, a set of appliances and an archwire are provided for both the upper and the lower dental arch of the patient, and treatment of both arches is carried out at the same time.

Today, there are numerous methods for selecting orthodontic appliances and archwires, and the particular selection method used by practitioner is related to the type of orthodontic techniques that are expected to be employed during the course of orthodontic therapy. For example, one popular technique is known as the "straight wire" technique, and involves the use of brackets having slots that are designed to be in a common plane once the teeth have moved to desired, final positions. Although the slots of the brackets are not aligned at the beginning of treatment due to the various malpositions of the teeth, the inherent resilience of the archwire provides a restoring force that tends to move the archwire and hence the slots of the associated brackets into alignment in a common plane.

In the straight wire technique described above, each of the selected brackets has a certain "prescription" that represents particular characteristics of the bracket. The prescription can include numerous different aspects or features of the bracket, such as the size of the archwire slot, as well as orientation of the slot relative to a base of the bracket that is intended to be mounted on the tooth surface. The prescription describing the orientation of the archwire slot relative to the base may include values for torque, angulation and rotation. In terms of tooth movement, "torque" is often described as tipping movement of the long axis of the tooth in a buccolabial-lingual direction (i.e., in directions toward and away from the patient's lips or cheeks and the patient's tongue), "angulation" is often described as tipping movement of the long axis of the tooth in mesial and distal directions (i.e., in directions toward and away from the center of the patient's dental arch) and "rotation" is often described as rotational movement of the tooth about its long axis.

The prescription of orthodontic brackets often varies from tooth to tooth. For example, many practitioners prefer that the long axes of the lower anterior teeth be as upright as possible, and consequently will prescribe for those teeth a bracket having torque and angulation values that are relatively small. In contrast, the upper central incisor teeth normally have long axes that are slanted. As a result, the practitioner will prescribe upper central brackets having torque and angulation values that are somewhat greater. However, the desired prescription may change from one orthodontist to the next. Moreover, in some instances the prescription is varied from the practitioner's normal practice in order to accommodate the initial position of a tooth, the location of adjacent teeth or the orientation of opposing teeth for a particular patient.

Another type of orthodontic brace is known as a positioner, and comprises an elastomeric material that is formed in the shape of a tray. The tray has a series of adjoining cavities for receiving the teeth. Each tooth is received in a respective cavity, and the resilient nature of the elastomeric material tends to shift the teeth to desired positions. An example of an orthodontic positioner is described in U.S. Pat. No. 5,055,039.

Orthodontic positioners are often made in the laboratory from a sheet of elastomeric material. One method of making a positioner includes an initial step of making an impression of the patient's dental arch using an impression material. A model of the patient's existing dental arch is then made from the cured impression. Next, teeth of the model are cut away and repositioned in wax in desired orientations. The sheet of elastomeric material is then molded over the repositioned model teeth in order to create a custom tray. The elastic material is resilient and has inherent memory, but preferably is sufficiently stiff in order to exert gentle pressure on the teeth when the tray is placed over the patient's dental arch. The pressure by the tray on the teeth tends to shift the teeth toward desired positions over a period of time.

U.S. Pat. No. 5,975,893 describes a method for incrementally moving teeth using a series of polymeric trays in successive order. The trays are designed by a computer to provide a plurality of different, intermediate tooth arrangements as well as a final tooth arrangement. Each tray is sufficiently resilient to provide corrective forces in order to move the teeth in relatively small increments and toward the desired, final tooth arrangement.

In the past, orthodontic practitioners have often selected prescriptions for braces by their first-hand knowledge of past treatment results with other patients and by reviewing results reported in the literature. However, some patients present unique problems, and reference to techniques that have been satisfactorily used in the past may not be suitable for certain patient's in the future. For example, a force module may be desired in a particular instance to assist in moving the teeth, and the force module may affect the final positions of the teeth to such a degree that the prescription should be changed.

Moreover, the problem of selecting an orthodontic prescription is aggravated by the nature of orthodontic treatment because the results of treatment may not be apparent for some time. Tooth movement is carried out slowly during orthodontic therapy, in order to reduce the amount of pain experienced by the patient and also to give sufficient time for the bone to grow and fix each tooth in place in its new position. As a result, practitioners prefer to make certain that the prescription of the brace that is initially selected is satisfactory for moving the teeth to desired, final orientations.

In addition, it is sometimes difficult for practitioners to predict the effects of tooth movements when a change in the prescription of the brace is made. The problem of predicting tooth movement is compounded by the fact that the roots of the teeth are not visible in ordinary view. Furthermore, spatial cognition of tooth movement in three dimensions is difficult, especially when such tooth movement may be influenced by the positions of adjacent teeth along the dental arch.

As can be appreciated, it would be desirable to provide a system for facilitating the selection of a custom orthodontic brace, and in particular to provide a system for facilitating the selection of a prescription for a custom orthodontic brace. Preferably, such a system would be easy to use and would facilitate the understanding of long-term effects of the particular brace selected. Moreover, such a system should be adaptable for use with any type of brace, including positioners, a series of custom trays, systems that include brackets and archwires as well as other types of braces.

SUMMARY OF THE INVENTION

The present invention is directed toward methods and apparatus that facilitate the selection of a custom orthodontic brace. In accordance with one aspect of the invention, images of the teeth are displayed in orientations representing final orientations at the conclusion of treatment with a first brace, as well as in orientations representing final orientations at the conclusion of treatment with a second brace. The images representative of results obtained from both the first brace and the second brace are simultaneously displayed, preferably in contrasting images, so that the relative effects of the two braces on the resulting positions of the teeth can be easily observed. In this manner, the practitioner can better understand the cause and effect relationship between the selected brace and the final or finish positions of the corresponding teeth.

In accordance with another aspect of the invention, images of teeth are displayed in orientations during a stage of orthodontic treatment that precedes a final stage. The stage may be an initial stage or an intermediate stage. Images of the teeth are also displayed in orientations representing final orientations at the conclusion of treatment with a certain brace. The images in the finished position and in the preceding stage position are simultaneously displayed, also preferably in contrasting images, so that the effect of the certain brace on the teeth can be readily observed.

In more detail, the present invention is directed in one aspect to a method of selecting a custom orthodontic brace. The method comprises:

providing a set of data representative of a number of teeth of a dental arch;

selecting a first orthodontic brace for at least some of the teeth in the dental arch, wherein the first brace has a certain prescription;

determining first positions of the teeth as they might appear when the first brace is mounted on corresponding teeth;

selecting a second orthodontic brace for at least some of the same teeth in the dental arch, wherein the second brace has a prescription that is different than the prescription of the first brace;

determining second positions of the teeth as they might appear when the second brace is mounted on corresponding teeth; and simultaneously displaying an image of at least one tooth when in the first position and when in the second position, wherein at least part of the images are overlaid, and wherein at least a portion of any difference in the orientations of the displayed tooth images between the first position and the second position appears in contrast so that the relative effect of the first brace and the second brace can be observed.

Another embodiment of the present invention is also directed to a method of selecting a prescription for an orthodontic brace. In this embodiment, the method comprises:

providing a set of data representative of a number of teeth of a dental arch;

selecting a first orthodontic brace for at least some of the teeth in the dental arch, wherein the first brace includes a first set of appliances comprising an archwire and a number of brackets, and wherein each appliance of the first set has a certain prescription;

determining first positions of the teeth as they might appear when the first brace is mounted on corresponding teeth;

selecting a second orthodontic brace for at least some of the teeth in the dental arch, wherein the second brace includes a second set of appliances comprising an archwire and a number of brackets, wherein each appliance of the second set has a certain prescription, and wherein at least one appliance of the second set has a prescription that is different than the prescription of one of the appliances of the first set;

determining second positions of the teeth as they might appear when the second brace is mounted on corresponding teeth; and simultaneously displaying an image of at least one tooth when in the first position and when in the second position, wherein at least part of the images are superimposed with respect to each other, and wherein at least a portion of any difference in the orientations of the displayed images between the first position and the second position appears in contrast so that the relative effect of the first brace and the second brace can be observed.

Another aspect of the present invention is also directed to a method of selecting a custom orthodontic brace. This method comprises:

providing a set of data representative of a number of teeth of a dental arch;

displaying at least one tooth of the dental arch as a first image in an orientation as it appears during one stage of orthodontic treatment that precedes a final stage of orthodontic treatment;

selecting a certain group of orthodontic appliances for the dental arch, wherein the certain group of appliances includes an archwire having a certain prescription and a number of brackets, each of the brackets of the certain group corresponding to one of the teeth and having a certain prescription;

determining finish positions of the teeth as they might appear when the brackets of the certain group are mounted on corresponding teeth, the archwire of the certain group is connected to the brackets of the certain group and the teeth have moved in response to forces exerted on the brackets of the certain group; and displaying at least one tooth in its determined finish position as an image, wherein at least a portion of any difference in the orientations of the teeth in the displayed finish positions appears in an image that contrasts with the image of the teeth in the displayed preceding stage positions so that the effect of the certain group of appliances can be observed.

An additional aspect of the present invention is also directed to a method of selecting a custom orthodontic brace. This method comprises:

providing a set of data representative of a number of teeth of a dental arch;

displaying at least one tooth of the dental arch as a first image in an orientation as it appears during a first stage of orthodontic treatment;

selecting a brace for the dental arch, wherein the brace has a certain prescription;

determining second positions of the teeth as they might appear when the brace is mounted in the oral cavity and the teeth have moved in response to forces exerted by the brace; and displaying at least one tooth in its second position as an image, wherein any difference in the orientations of the teeth in the displayed second positions appears as an image that contrasts with the image of the teeth in the displaced first positions so that the effect of the brace can be observed.

Yet another aspect of the present invention is directed toward a method of manipulating data of a dental patient's tooth. This method comprises:

obtaining a first set of data representing the shape of at least a portion of a patient's tooth;

providing a second set of data that represents the shape of at least a portion of a model tooth that is of the same type of tooth as the tooth represented by the first set of data;

manipulating at least some of the data of at least one of the first set of data and the second set of data so that the scale of the patient's tooth and the scale of the model tooth are substantially the same; and combining at least some data of the first set and of the second set in order to obtain a third set of data that represents at least part of the model tooth and at least part of the patient's tooth.

The present invention is also directed in another aspect to a computer readable medium that tangibly embodies a program executable for performing selection of a prescription for an orthodontic brace. The computer readable medium comprises a set of data representative of a number of teeth of the dental arch, and first means for displaying images of at least some of the teeth in first positions as they might appear when a first brace is mounted on the teeth. The computer readable medium also comprises second means for displaying images of at least some of the teeth in second positions as they might appear when a second brace is mounted on the teeth. The second means includes means for simultaneously displaying at least some of the images of the same teeth in the second positions and the first positions. At least part of the images of the displayed teeth in the first position and in the second position are superimposed.

The present invention is also directed in another aspect to a computer readable medium that tangibly embodies a program executable for performing selection of a prescription for an orthodontic brace. In this aspect, the computer readable medium comprises a set of data representative of a number of teeth of the dental arch, and first means for displaying images of at least some of the teeth in positions as they might appear during a first stage of orthodontic treatment. The computer readable medium also comprises second means for displaying images of at least some of the teeth in second positions as they might appear when a certain group of orthodontic appliances is mounted on the teeth. The second means includes means for simultaneously displaying at least some of the same teeth in the first stage positions and in the second stage positions. At least part of the images of the displayed teeth in the first stage positions and in the second stage positions are superimposed.

Additional features and advantages of the invention are set out below in the paragraphs that follow and are described with reference to the accompanying drawings.

BRIEF DESCRIPTION OF THE DRAWINGS

FIG. 2 is a front elevational view of an example of one type of orthodontic brace that is mounted on an upper dental arch of a patient, and in this instance the brace includes a number of brackets along with an archwire received in the slots of each bracket;

FIG. 3 illustrates an example of one type of display of information that is provided by the present invention for assisting in the selection of an orthodontic brace prescription;

FIG. 4 is an enlarged, side elevational view taken through a portion of the image shown in the display of FIG. 3;

FIGS. 8-10 are front elevational, side elevational and bottom views respectively of a model tooth, illustrating an example of creation of the coordinate system described in FIGS. 5-7;

DETAILED DESCRIPTION OF THE PREFERRED EMBODIMENTS

Figure 1:
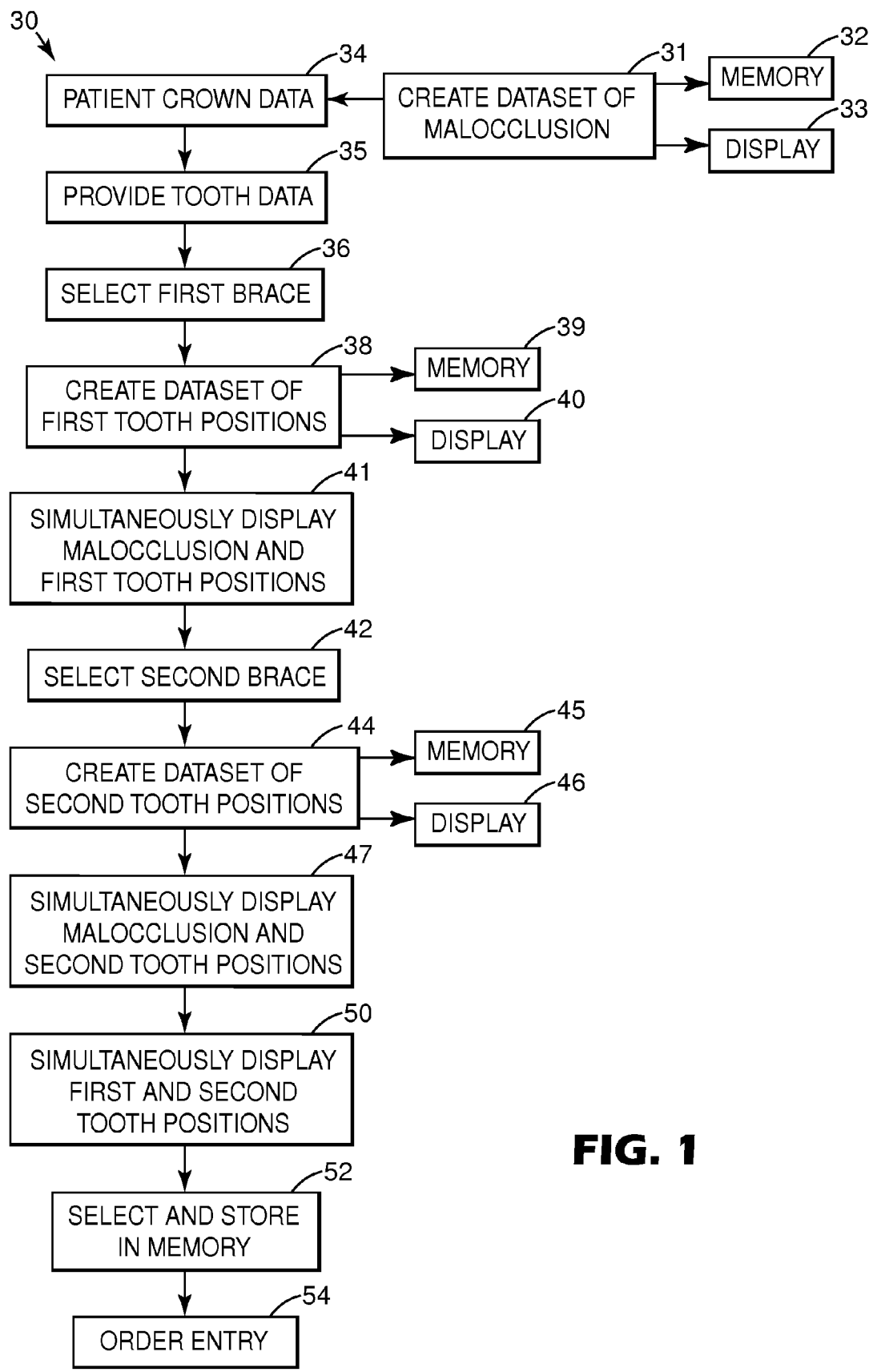
FIG. 1 is a block diagram showing the overall steps of a computer program for selecting a prescription of an orthodontic brace according to one embodiment of the invention.

A method of selecting a custom orthodontic brace according to the present invention is broadly described by the flow diagram shown in FIG. 1 and is designated by the numeral 30. The method includes the act of creating a dataset that is representative of the patient's maloccluded teeth (Block 31). The dataset may be obtained by any suitable means known in the art.

For example, the dataset representative of the maloccluded teeth may be created through the use of an intra-oral camera that is held in the patient's oral cavity, or by the use of X-ray apparatus or other type of radiation apparatus. Alternatively, the set of electronic data may be obtained by the use of a contact probe that engages the surface of the patient's teeth at a multitude of locations.

As another alternative, the data representative of the patient's maloccluded teeth may be obtained by first taking an impression of the patient's teeth using a curable impression material. Next, a dataset is obtained by scanning the impression with a camera or other device, or by use of the apparatus described in PCT published application number WO 97/03622. As another option, a stone model may be made from the resulting impression, and the dataset is then obtained by scanning the model, by use of a mechanical profilometer that mechanically probes the model or by use of the apparatus described in PCT application WO 97/03622.

The dataset representative of the maloccluded teeth is stored in memory as indicated in Block 32. Optionally, the maloccluded teeth are displayed as a visual image as shown by Block 33. The image is preferably displayed on a computer monitor, although other methods of showing or displaying the information are also possible. For example, the images may be printed by a printer or projected onto a screen.

Next, and as shown by Block 34, data separately representing each of the patient's tooth crowns is obtained. The individual crown data is obtained by segregating the data representing the maloccluded teeth into individual datasets representing each tooth. Each tooth is identified by tooth type, such as a lower right first molar or an upper left cuspid. The teeth may be identified by input from the practitioner. For example, a program may be provided that enables the practitioner to position the curser over the image of the maloccluded teeth on a computer monitor and then select or input the appropriate tooth identity. Alternatively, the computer can assign an identity to each tooth in sequential order along the dental arches, after the practitioner verifies that all of the expected teeth are present in the image.

As depicted in Block 35, a set of data representing the individual teeth is then obtained from data representing the individual crowns. Preferably, the data representing the teeth as indicated in Block 35 includes the entire structure of the tooth, including all portions of the tooth root or roots. This set of data may be created by any suitable means. For example, this set of data could be provided by selecting certain data from a library of generic tooth model data. Optionally, the practitioner could select a model tooth having a crown that is similar in size and configuration to the patient's corresponding actual tooth crown. For instance, if the patient has an upper left lateral tooth with a crown that is relatively narrow, a model of an upper left lateral tooth having a crown with a similarly narrow shape is selected from a plurality of model upper lateral teeth.

As another example, the data representative of teeth as set out in Block 35 may be provided by use of data for a model tooth that is scaled in dimensions as needed to relative dimensions corresponding to the patient's actual tooth. In this example, data representing a tooth model is obtained from a library of teeth. The data is then changed as needed to increase or decrease the size of the tooth model along one or more references axes until the tooth model is similar in size and/or shape of the corresponding tooth of the patient.

The scaling operation (i.e., the manipulation of the data to increase or decrease of the model tooth along one or more axes) may be carried out by the practitioner by visual comparison of the image of the model tooth to the appearance of the patient's actual tooth. Alternatively, the scaling operation may be carried out by software that adjusts the dimensions of the model tooth along one or more axes in response to a comparison of electronic data representative of the patient's actual tooth. The scaling process is carried out for each tooth in the dental arch as needed.

Optionally, data representative of the crowns of the patient's actual teeth may be married to data representing the roots of model teeth that are selected from a library of tooth roots. If desired, the data representing the tooth root models may be changed as needed corresponding to directions along one or more reference axes until the tooth root model is similar in size and/or shape of the corresponding tooth root of the patient or until it is appropriate in size and/or shape for mating with the corresponding crowns. The scaling operation of the tooth root may be carried out as described above.

Preferably, the act of providing a set of data representative of a number of teeth of a dental arch as indicated by Block 35 includes the act of providing data that represents or at least approximates the surface of the teeth. The surface data could be part of a solid model, a model that has been surfaced, a wire frame model or a model with point cloud surface data. It is preferable that surface data is utilized in the steps below in order to provide an image that is closely similar to the appearance of natural teeth.

A first orthodontic brace is then selected as shown by Block 36. The brace may be of any suitable type desired by the practitioner. For example, the first brace may be a system of slotted orthodontic brackets along with an archwire that is received in the slots of the brackets. In that instance, the practitioner would also select the prescription of the brackets and the archwire.

The prescription for the orthodontic bracket may include any one or more of a number of values that represent certain structural features, dimensional characteristics, material properties or other aspects of the bracket. For example, the prescription may include values representing the torque, angulation and rotation provided by the bracket. The prescription of the bracket may also include an "in/out" value which may represent, for example, the shortest distance between the lingual side of the archwire slot and the outwardly-facing side of the bracket base that is intended to contact or be closely adjacent the surface of the patient's tooth. The prescription for the bracket may also include other aspects such as the labial-lingual depth of the archwire slot, the occlusal-gingival width of the archwire slot and the mesial-distal length of the archwire slot. The prescription of the bracket may also optionally include the material of the bracket and/or the material of the structure defining the archwire slot (such as an archwire slot liner), and the type or classification of appliance (i.e., a "Begg" bracket, a twin bracket, or a bracket with rotation wings). The prescription of the bracket may also include linear and/or angular tolerances of the various dimensions and angulations.

The prescription for an archwire may similarly include any one or more of a number of values that represent certain structural features, dimensional characteristics, material properties or other aspects of the archwire. For example, the prescription may include values that represent the shape of the archwire, such as the cross-sectional shape (whether round, rectangular or square) as well as its overall shape when in its normally relaxed configuration (i.e., whether it lies in a flat plane when relaxed or whether it is constructed to have a reverse curve of Spee when relaxed). Moreover, the prescription of the archwire may include its overall dimensions when relaxed as well as its cross-sectional dimensions (such as its diameter for an archwire having a round cross-sectional configuration, and its width and depth for archwires having a rectangular cross-sectional configuration). The prescription for the archwire may also include its composition, stiffness and/or values representing frictional characteristics of the archwire in use.

As used herein, the word "bracket" shall include brackets for the patient's anterior, cuspid and bicuspid teeth as well as orthodontic tubes such as buccal tubes. Buccal tube brackets are typically mounted on the patient's molar teeth and receive ends of the archwire. Optionally, the buccal tubes are convertible. In convertible tubes, the tubular passage may be "opened" by the practitioner when desired to create a slot that is open along one side, such as along its buccolabial side.

An example of a system of brackets and archwires is illustrated in FIG. 2. In FIG. 2, a dental arch 60 of a patient is shown along with a first brace 62. The first brace 62 comprises a set of brackets 64, each of which is bonded to a respective tooth 66 of the dental arch 60. Buccal tube brackets 68 are mounted on molar teeth of the dental arch 60. The brackets 64, 68 have slots or grooves that receive an archwire 70. Although only an upper dental arch is depicted in FIG. 2, it should be understood in this regard that a brace similar to the brace 62 may be affixed to the patient's lower dental arch.

The archwire 70 is secured to the brackets 64, 68 by ligating structure, such as wire ties or the tiny elastomeric O-rings shown in FIG. 2. Alternatively, the brackets 64, 68 may be of the type known as "self-ligating" brackets that include sliding clips, shutters or other type of latches to retain the archwire 70 in place. The archwire 70 forms a track to guide movement of the brackets 64, 68 as well as the associated teeth toward positions as selected by the practitioner.

As an alternative, the first orthodontic brace may be something other than a system of brackets and archwires. For example, the first brace may be an orthodontic positioner. Examples of suitable positioners are described in U.S. Pat. Nos. 5,055,039 and 5,975,893, both of which are expressly incorporated by reference herein.

The orthodontic positioner as selected by the practitioner will have a certain prescription comprised of one or more aspects. Examples of those aspects include the location, orientation and/or shape of recesses in the positioner that receive the patient's teeth when the positioner is in place in the oral cavity. Other aspects of the prescription may include the stiffness of the material of the positioner, the composition of the material and the size and placement of void spaces, if any.

Next, a dataset of first positions of the teeth is created as set out in Block 38. The first positions of the teeth are representative of the tooth orientations as they might appear when the first orthodontic brace is connected with the tooth models as set out in Block 32 and the model teeth have moved to a final arrangement in response to forces exerted on the teeth. In practice, the tooth models and the first brace need not be physically connected together or even associated with each other in an image. Instead, it is only necessary that the dataset representing the first positions of the teeth represent the final positions that those teeth will assume or closely assume if, hypothetically, the first brace is constructed in physical form and is mounted or otherwise connected to the patient's actual teeth. An example of one method for determining the first positions of the teeth is described in a subsequent section below. Preferably, the dataset of final positions of the teeth is stored in memory as indicated by Block 39. Preferably, the storage and memory shown in Block 39 as well as in Block 32 are retained in a data file (or associated with a data file) that contains other information relating to the particular patient, such as information relating to dental or medical history, other information pertaining to the patient's dentition and/or information relating to the patient's address, emergency contacts and account.

The final positions of the teeth are also optionally displayed as indicated by Block 40. The information may be made known by displaying the information on a screen, by printing the information onto hard copy by a printer, or otherwise communicated to the user. For example, the practitioner may elect to see numerical data that represents the orientation of some or all of the teeth when in the final position. In this example, the practitioner may be interested in knowing, for instance, whether or not the lower left cuspid has been rotated to a particular angular rotation under the influence of the first brace. If the practitioner is satisfied with the displayed final positions of the teeth, the selection of a second brace for purposes of comparison may be omitted.

Preferably, and as indicated by Block 41, images are provided to the practitioner that show at least one tooth when in a first position and simultaneously show at least one tooth when in a second position. Optionally, but not necessarily, the first position represents the "original" position of the tooth before orthodontic treatment, and the second position represents the "final" position of the tooth at the conclusion of orthodontic treatment. However, other alternatives are also possible. For example, the first position and/or the second position may be a position of the tooth at a certain intermediate stage of treatment. The images are preferably displayed on a computer monitor, although other methods of showing or displaying the information are also possible. For example, the images may be printed by a printer, projected onto a screen or shown by other means.

At least part of the images are overlaid or superimposed with respect to each other, so that at least one tooth when in the first position is displayed either directly over or under the same tooth when in the second position. As such, any difference in the orientations of the displayed tooth images between the first position and the second position can be readily compared. The difference in positions is an indication of the therapeutic effect of the first brace over a period of time.

Preferably, any difference in the orientations of the displayed tooth images between the first position and the second position appears in contrast to facilitate visual identification of the effect of the first brace. For example, the contrast in images may appear as a color contrast on the monitor, screen or printed copy. In this example, an image of a model tooth in the first position may appear as red and an image of the model tooth in the second position may appear as green.

As another alternative, the contrast in the images may appear as a difference in the type of shading used to represent the surface of the tooth when in the first position and in the second position. In this example, the surfaces of the images may include a series of diagonal lines for the tooth in the first position and a cross-hatched pattern of lines for the tooth in the second position. As another alternative, the contrast in images may appear as a difference in the appearance of the perimeter of the images, such as dashed lines or red lines for the perimeter of the tooth in one position and dotted lines or green lines for the perimeter of the tooth in the other position.

As an additional alternative, the contrast in images may appear as a result of overlaid portions of two transparent or semi-transparent images. For example, one image may be a semi-transparent first color and the second image may be a semi-transparent second color. When the first color and the second colors are overlaid, a third color appears which results in a color contrast between the first color and the second color. The same effect may be carried out by other methods as well, such as by use of two different cross-hatchings that, when combined, create a third cross-hatching with a somewhat different appearance.

FIG. 3 is an example of the simultaneous display of images of teeth 66a, 66b in the first and second positions. For exemplary purposes, the teeth 66a shown in FIG. 3 in the first position have surfaces that are drawn as plain surfaces, while the teeth 66b shown in FIG. 3 in the second position have surfaces that are drawn with stippling. As can be appreciated by reference to FIG. 3, the differences in appearance of the images of the first and second positions of the teeth 66a, 66b along the dental arch are very apparent and greatly facilitate an understanding of the therapeutic effect of the first brace after the teeth have moved to second positions. Although the differences in positions shown in FIG. 3 are represented by plain surfaces in comparison to stippled surfaces, it is presently preferred to display the images as solid objects in contrasting colors on a color computer monitor or other form of color display output in order to highlight the effect or result obtained by the first brace.

FIG. 4 is a side elevational view, taken across a middle portion of a tooth 66a of the dental arch shown in FIG. 3. The tooth image 66a shows the tooth in its first position, while the tooth image 66b shows the tooth in its second position. Preferably, the computer and its associated display output can be instructed to show the relative differences of the first position and the second position for any one of the teeth in the dental arch, as may be desired to facilitate understanding of the effect of the first brace. Moreover, it is preferred that the computer and associated display output be capable of displaying the tooth 66a along any one of a number of reference planes other than the reference plane selected for exemplary purposes in FIG. 4.

As illustrated in FIGS. 3 and 4, the contrasting images 66a, 66b that simultaneously show the first and second positions are especially useful as an aid to understanding movement of the roots of the teeth which are not visible by the naked eye during the course of treatment. For example, a small amount of torque as effected by a selected bracket may not produce significant differences in the relative positions of the visible portions of the tooth (i.e., the crowns of the teeth). However, the difference between the first and second position of the same tooth along its root may be substantial. By displaying the entire length of the tooth in the first and second positions, the practitioner is able to easily assess the effect of the first brace and thereby increase the likelihood that the chosen brace meets the desired outcome of treatment.

Optionally, and as indicated in Block 42, the practitioner selects a second orthodontic brace for comparison to the first selected brace. The second selected brace may be somewhat similar to the first selected brace, or may be substantially different from the first selected brace.

For example, the first and second braces may both include a system of brackets and archwires, where the only difference between the first and second brace is one component of the prescription of one bracket. For instance, the first and second brace may be exactly the same except that the lower first right bicuspid bracket in the first set may have an torque of 12 degrees, and the lower first right bicuspid bracket of the second set may have an torque of 17 degrees. However, the prescription may also differ in other aspects, such as the rotation, angulation or any of the other aspects mentioned above.

Furthermore, the second orthodontic brace may be of a type different than the first orthodontic brace. For example, the second orthodontic brace may be a positioner, and the first orthodontic brace may be a system of brackets and an archwire. Other combinations and variations are also possible.

A set of electronic data is also created that represents second positions of the teeth, as indicated by Block 44. The second positions of the teeth are representative of positions of the teeth as they might appear when the second orthodontic brace is mounted on the patient's teeth and the teeth have moved to a second (and optionally a final) tooth arrangement under the influence of the second brace. The dataset of the second positions can be created in a manner similar to the creation of the dataset representative of the first positions as described above.

Preferably, the dataset created in Block 44 is stored in memory as indicated by Block 45. In addition, the second positions of the teeth are optionally displayed as indicated by Block 46. Blocks 45 and 46 may be carried out in a manner similar to the acts indicated by Blocks 39 and 40 respectively, as described above. Optionally, the individual displays indicated by Blocks 33 and 46 are also shown simultaneously, as indicated by Block 47. The simultaneous display as set out in Block 47 is carried out with contrasting images in a manner similar to the simultaneous display described above with reference to Block 41.

Typically, the individual displays of the second tooth positions as indicated by Blocks 40 and 46 are displayed simultaneously, as indicated by Block 50. Consequently, the display set out in Block 50 includes a visual image of the predicted final positions of the teeth when subject to treatment by the first brace as well as a visual image of the predicted second final positions of the teeth when subject to treatment by the second brace. The simultaneous display set out in Block 50 is carried out with the use of contrasting images in the manner similar to the simultaneous, contrasting images described above with reference to Block 41.

From the simultaneous display of the images as represented by Block 50, the practitioner can then select the brace that best meets the goals of treatment. Block 52 represents the selection by the practitioner, and may be carried out by keystroke entry input or by manipulating a mouse that can be "clicked" once the computer cursor is placed over the image of the selected brace. The identification of the selected brace is stored in memory, and preferably retained in a data file or associated with a data file that contains other information relating to the particular patient, such as the various information described above in connection with Blocks 42 and 44.

Optionally, a computer can then be used to purchase the selected brace or components of the brace in automated fashion to add to a list of items to be purchased from a vendor. For example, the computer used by the practitioner for the previous acts set out in Blocks 31 to 52 may be electronically associated (e.g., by modem) with a server of the manufacturer or distributor. The purchase is preferably carried out with a computer-generated purchase order or order form that uses, at least in part, digital data corresponding to one or more components of the selected brace. For example, the purchase order may include a list of brackets and one or more archwires, each having a certain prescription. Optionally, the computer may be programmed to first check the existing inventory of the practitioner to determine if the selected brace (or its components) are on-hand, and to earmark such brace for use with the patient if the answer is in the affirmative.

Alternatively, the first positions of the teeth may be representative of tooth orientations as they might appear in an initial or intermediate stage of orthodontic treatment, and the second positions of the teeth may be representative of tooth orientations as they might appear during a subsequent intermediate stage of orthodontic treatment or at a final or finished stage of orthodontic treatment. In this example, the practitioner may be interested in studying the effect of a certain orthodontic brace when mounted on the patient's teeth and observing movement of the teeth as a result of the brace. In this example, the selection of a second orthodontic brace is optional, although may also be desired for purposes of comparing the relative effects of two different braces.

The preceding paragraphs have set out examples of methods and apparatus for selecting a prescription for an orthodontic brace. In the paragraphs that follow, an example is described of one method of determining final tooth positions according to the prescription of the brace selected for review by the practitioner. In order to determine final tooth positions, geometric references are first established on each tooth and on an arch form. From those geometric references, virtual dentition and occlusion are created.

Creation of Geometric Reference on Tooth

This section describes the attachment of a coordinate system to a tooth. Teeth, by their nature, have a complex geometry, and the outer surface of the tooth (such as its labial surface) usually does not have a shape of a simple curve. Instead, the radius typically changes as different portions of the tooth surface are approached.

The coordinate system as described in this section is tangent in the mesial-distal plane, tangent in the occlusal-gingival plane and normal to those two planes over a given perimeter. The perimeter selected can be very small or relatively large. For example, the perimeter can be 0.0001 inch (0.0025 mm), or alternatively can be equivalent to the size of a bracket base. As another option, the perimeter can be anything between these two values, or larger or smaller.

Figure 5:
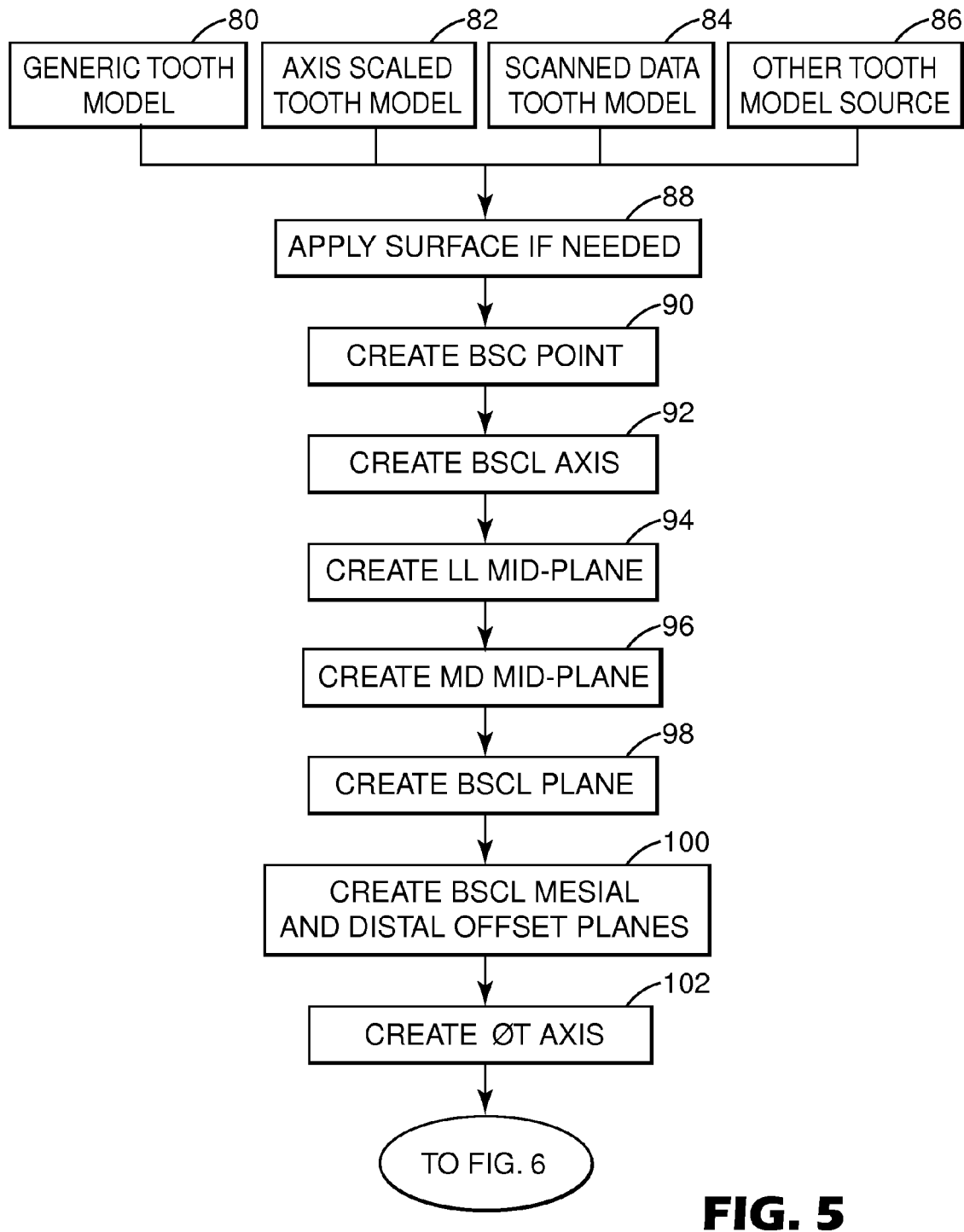
FIGS. 5-7 is a more detailed block diagram of a portion of the program shown generally in FIG. 1 and relates to the creation of a geometric reference on model teeth.
Figure 6:
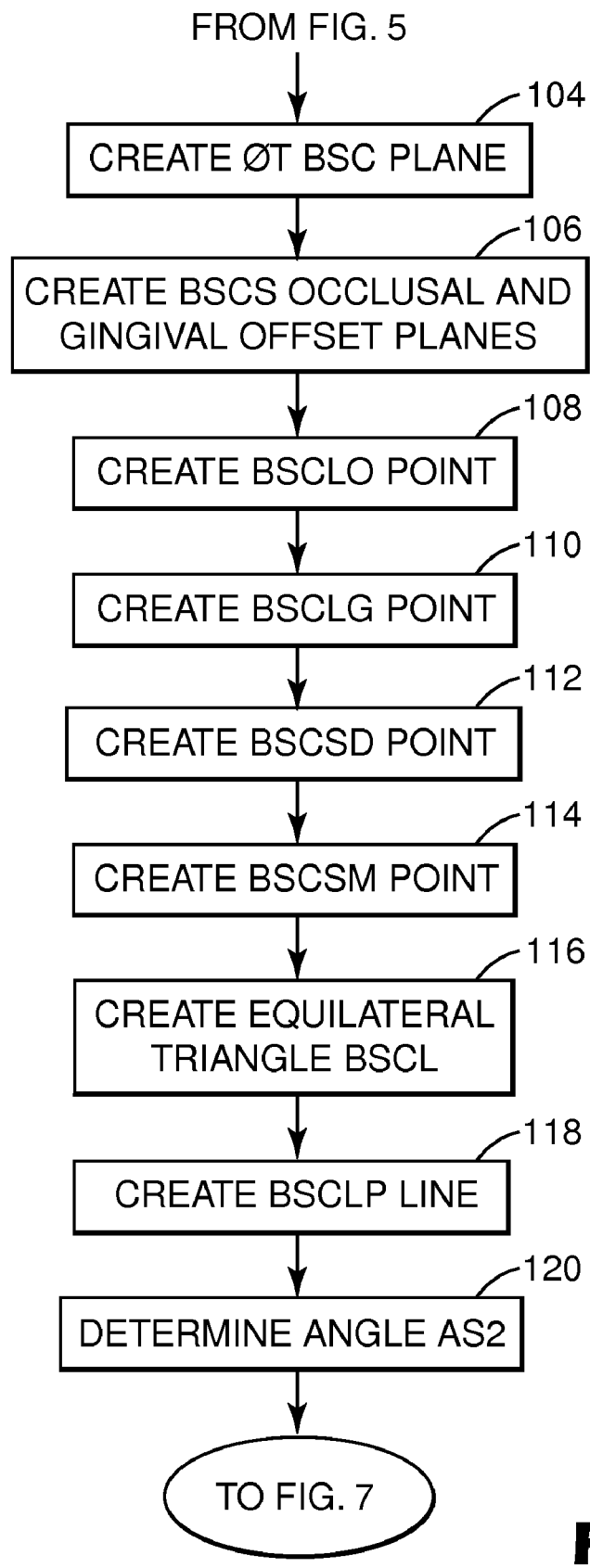
Figure 7:
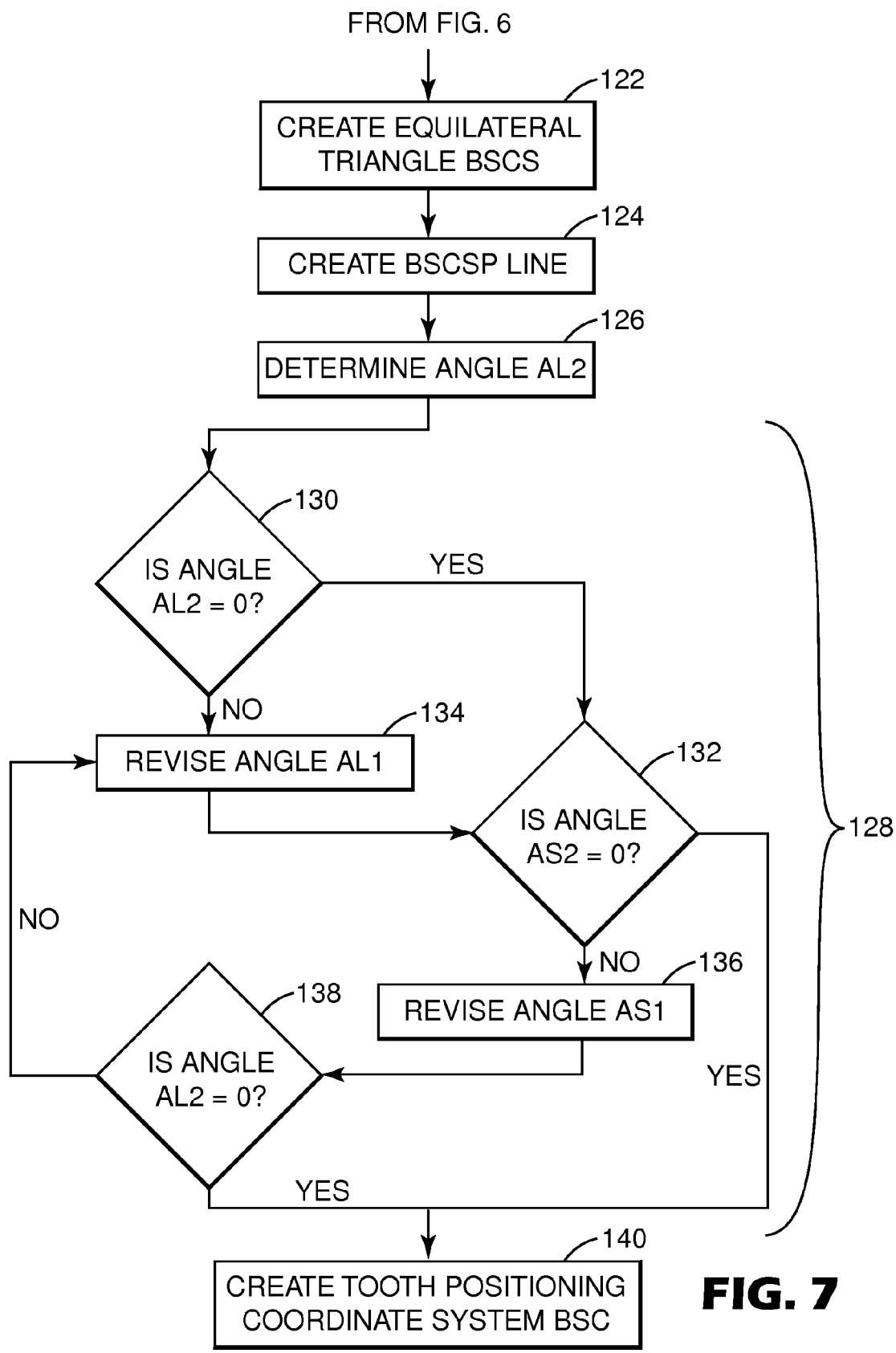

FIGS. 5-7 illustrate flow charts of a computer program for creation of a geometric reference on a tooth. The computer program automatically creates the coordinate system once a center point, or "BSC" has been entered into the program.

Table 1 sets out a definition of various abbreviations that are provided in the paragraphs that follow.

TABLE 1

| ABBREVIATION | TERM |
| --- | --- |
| O | Occlusal |
| G | Gingival |
| M | Mesial |
| D | Distal |
| LL | Lingual-Labial |
| T | Torque |
| A | Angulation |
| R | Rotation |
| IO | In-Out |
| BSC | Bracket Slot Center |
| BSC Axis | Long Axis of Tooth |
| BSCL | Along O–G BSC Axis |
| BSCS | Along M–D BSC Axis |
| 0T | Zero Torque |
| LO | Offset From Long Axis |
| SO | Offset From Short Axis |

The method of creating a geometric reference on a tooth model begins by creation of a BSC point, or bracket slot center point as indicated in Block 90. The BSC point is established on a surface or approximation of a surface of a tooth model, such as the tooth models and surfaces described above in connection with Block 32. The BSC point is the center of the geometric reference that follows. The BSC point could be the center of the bracket when the bracket is mounted on an ideal location of the tooth surface as described by any orthodontic technique, such as the techniques described by Dr. Lawrence F. Andrews. Alternatively, the BSC point could be the center of a bracket that has been intentionally mispositioned. As such, the bracket need not be placed in any particular "ideal" location on the tooth surface in order to carry out the method described below. An exemplary BSC point is indicated by the numeral 90 in FIG. 8.

Next, a BSCL axis is created as indicated by Block 92. The BSCL axis is the same as the long axis of the tooth and is indicated by the numeral 92 in FIGS. 8 and 9. Subsequently, the LL mid-plane or labial-lingual mid-plane is created as indicated by Block 94. The LL mid-plane is created by extension of the BSCL axis (i.e., the BSCL axis lies in the LL mid-plane). The LL mid-plane is oriented such that the model tooth is divided into a lingual section and a labial section. The LL mid-plane is indicated by the numeral 94 in FIG. 10.

The MD mid-plane is then created as indicated by Block 96. The MD mid-plane is created by extending the BSCL axis in an orientation that is perpendicular to the LL mid-plane. The MD mid-plane divides the model tooth into a mesial section and a distal section. The MD mid-plane is indicated by the numeral 96 in FIG. 10.

The BSCL plane, or bracket slot center line plane, is then created as set out in Block 98. The BSCL plane passes through the BSC point, is parallel to the BSCL axis, and is created in an orientation that is approximately perpendicular to the surface of the model tooth immediately surrounding the BSC point. The BSCL plane is designated 98 in FIG. 10.

The BSCL plane is oriented at an angle designated "AL1" with respect to the MD mid-plane. The angle AL1 is designated by the numeral 99 in FIG. 10. A later calculation will correct this angle to an orientation that is exactly perpendicular to the desired, adjacent surface area of the model tooth.

The BSCL mesial and distal offset planes are then created as indicated by Block 100. The BSCL mesial and distal offset planes are parallel to the BSCL plane, and are offset by a distance designated SO, or offset from the short axis. The BSCL mesial and distal offset planes are each indicated by the numeral 100 in FIG. 10. FIG. 10 also depicts the distance SO in each instance.

The 0T axis, or zero torque axis, is then created as set out in Block 102. The 0T axis passes through the BSC point and is normal to the BSCL plane. The 0T axis is designated by the numeral 102 in FIG. 10. Next, and as indicated in FIG. 6, the 0T BSC plane is created as shown by Block 104. The 0T BSC plane passes through the 0T axis and is approximately perpendicular to the surface of the model tooth immediately adjacent and surrounding the BSC point.

The 0T BSC plane is designated 104 in FIG. 9. The 0T BSC plane is oriented at an angle designated AS1 with respect to the BSCL axis. Angle AS1 is designated by the numeral 105 in FIG. 9. A later calculation will correct the angle AS1 to an angle of exactly 90 degrees, or perpendicular to the desired tooth surface area.

Subsequently, the BSCS occlusal and gingival offset planes are created as set out in Block 106. The BSCS occlusal and gingival offset planes are parallel to the 0T BSC plane and are offset by a distance designated LO. The BSCS occlusal and gingival offset planes are designated by the numeral 106 in FIG. 8. FIG. 9 depicts the offset distances LO in each instance.

Next, and as shown in Block 108, the BSCLO point is created. The BSCLO is located at the intersection of the surface of the model tooth, the BSCL plane and the BSCS occlusal offset plane. The BSCLO point is designated by the numeral 108 in FIGS. 8 and 9.

Subsequently, the BSCLG point is created as shown by Block 110. The BSCLG point is located at the intersection of the surface of the model tooth, the BSCL plane and the BSCS gingival offset plane. The BSCLG point is identified by the numeral 110 in FIGS. 8 and 9.

The BSCSD point is then created as shown in Block 112. The BSCSD point is located at the intersection of the model tooth, the OTBSC plane and the BSCL distal offset plane. The BSCSD point is designated by the numeral 112 in FIG. 8.

The BSCSM point is then created as set out in Block 114. The BSCSM point is located at the intersection of the surface of the model tooth, the OSBSC plane, and the BSCL mesial offset plane. The BSCSM point is identified by the numeral 114 in FIG. 8.

Next, the equilateral triangle BSCL is created as described in Block 116. The BSCL triangle lies on the BSC plane. The first leg of the BSCL triangle extends from the BSCLO point (108) to the BSCLG point (110). The length of the first leg of the BSCL triangle is twice the distance of LO. The second and third leg of the triangle are of equal length and meet at a common point inside the model tooth. This common point is designated the BSCLP point 117 as illustrated in FIGS. 9 and 10.

Subsequently, the BSCLP line is created as shown by Block 118. The BSCLP line extends from the BSCLP point 117 to the BSC point 90. The BSCLP line is identified by the numeral 118 in FIG. 9.

The angle dimension AS2 is then created, as indicated by Block 120. The AS2 angle is measured from the projection of the BSCLP line and the 0T BSC plane onto the BSC plane. The angle dimension AS2 is indicated by the numeral 120 in FIG. 9.

With reference now to FIG. 7, the equilateral triangle BSCS is then created as set out in Block 122. The equilateral triangle BSCS lies on the 0T BSC plane. The first leg of this triangle extends from the BSCSM point (114) to the BSCSD point (point 112). The length of the first leg is twice the SO distance. The second and third leg of the triangle are of equal length and meet at a common point inside the model tooth. This new point is identified as the BSCSP point that is designated 123 in FIG. 10. FIG. 10 also illustrates the equilateral triangle BSCS, designated 122.

Next, and as set out in Block 124, the BSCSP line is created. The BSCSP line extends from the BSCSP point (123) to the BSC point (90). The BSCSP line is designated by the numeral 124 in FIG. 10.

The angle dimension AL2 is then created as set out in Block 126. The AL2 angle is determined from the projection of the BSCSP line (124) and the BSC plane onto the 0T BSC plane (104). The angle AL2 is identified by the numeral 126 in FIG. 10.

Block 128 in FIG. 7 represents steps taken by the computer program to correct error. In Block 130, the program determines whether angle AL2 is equal to zero degrees. If the answer is positive, the computer then determines whether the angle AS2 is equal to zero degrees as set out in Block 132. However, if angle AL2 is not equal to zero degrees, the angle AL1 is corrected as shown in Block 134 by adding the value of angle AL2 to the value of angle AL1. The computer then determines whether the angle AS2 is equal to zero degrees as set out in Block 132.

If angle AS2 is not equal to zero degrees, the angle AS1 is corrected as shown in Block 136. To correct angle AS1, the value of angle AS2 is added to the value of angle AS1. Next, the computer determines whether the angle AL2 is equal to zero degrees as shown by the Block 138. If the angle AL2 is not equal to zero degrees, the computer proceeds to the step indicated by Block 134 to correct the angle AL1 as described above.

Figure 11:
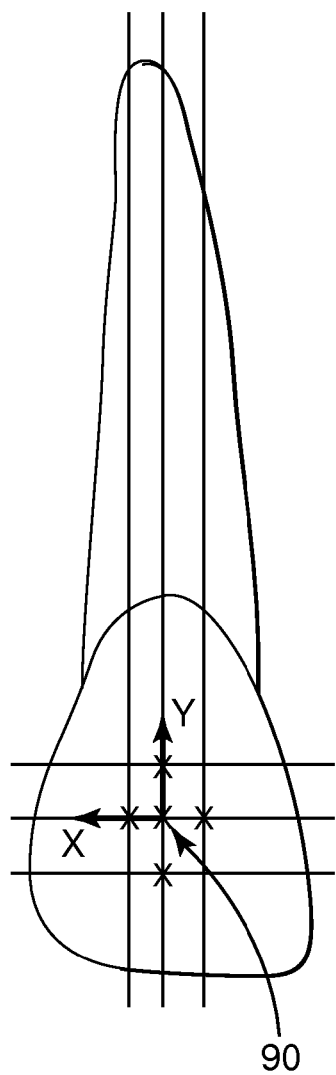
FIGS. 11-13 are front elevational, side elevational and bottom views respectively of an exemplary resulting tooth coordinate system obtained for an individual tooth using the program set out in FIGS. 5-7.
Figure 12:
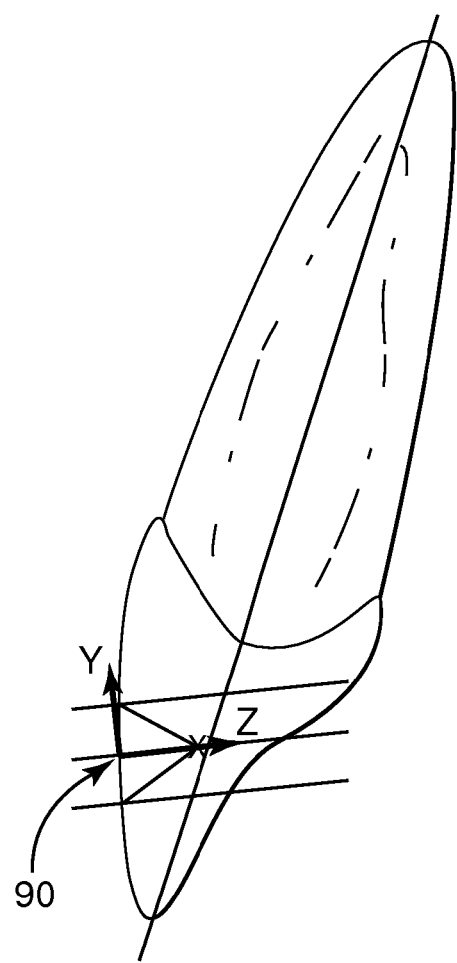
Figure 13:
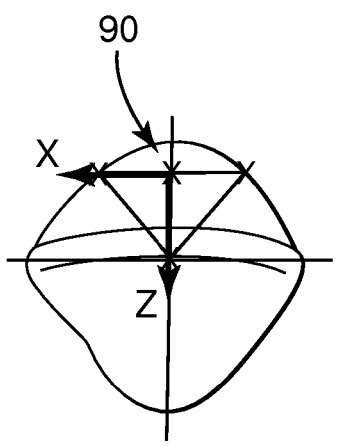

Once AL2 and AS2 are both equal to zero through block 128, the program proceeds to Block 140 where a tooth positioning coordinate system BSC is created. The BSC coordinate system is illustrated in FIGS. 11-13. The center of this coordinate system is located at the BSC point (90). The Y axis is parallel to the line formed by the BSCLO point and the BSCLG point, with a direction toward the gingival defined as a positive direction. The Z axis is perpendicular to the plane formed by the BSCLO point, the BSCLG point, the BSCSD point and the BSCSM point. In the Z axis, a direction toward the lingual is defined as a positive direction. The X axis of the BSC coordinate system is determined by following the right hand rule using the Y axis and Z axis.

Creation of Geometric Reference on an Arch Form

This section describes the attachment of a coordinate system to an arch form. Orthodontic archwires, for example, are often sold according to standardized shapes that have been developed over the years. Arch forms typically appear as a smooth curve that is symmetrical on either side of a midpoint, but the radius of curvature of the arch form typically varies along the length of the arch form.

The coordinate system described in this section is tangent to the arch form in the mesial-distal plane, and is parallel and normal to the occlusal plane over a given perimeter. The perimeter selected can be very small or relatively large. For example, the perimeter can be 0.0001 inch (0.0025 mm), or alternatively can be equal to the mesial-distal width of a bracket slot. As another option, the perimeter can be of any size between these two values.

Figure 14:
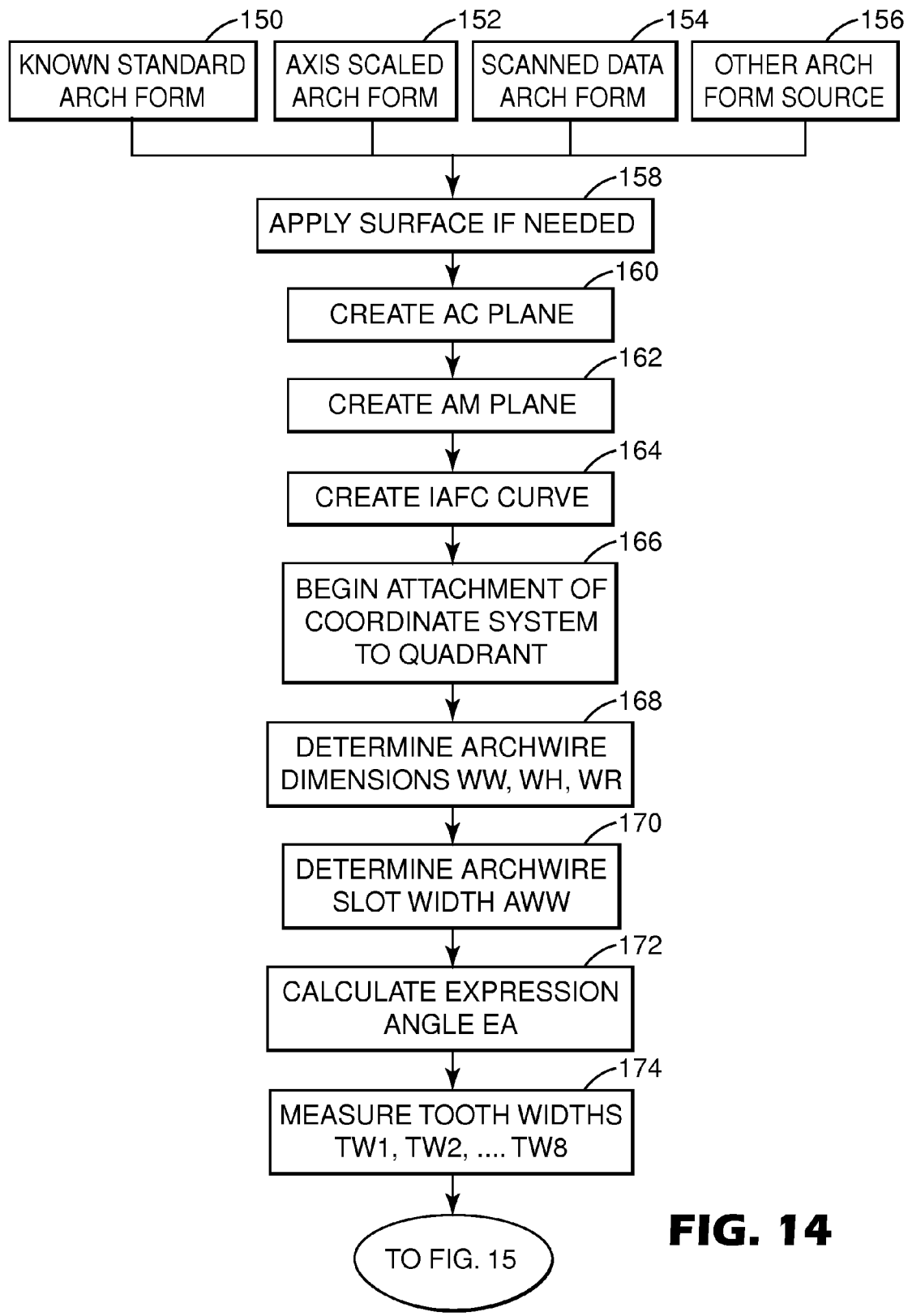
FIGS. 14-15 show a more detailed block diagram of another portion of the program of FIG. 1 and describe an example of a method for creating a geometric reference on an arch form.
Figure 15:
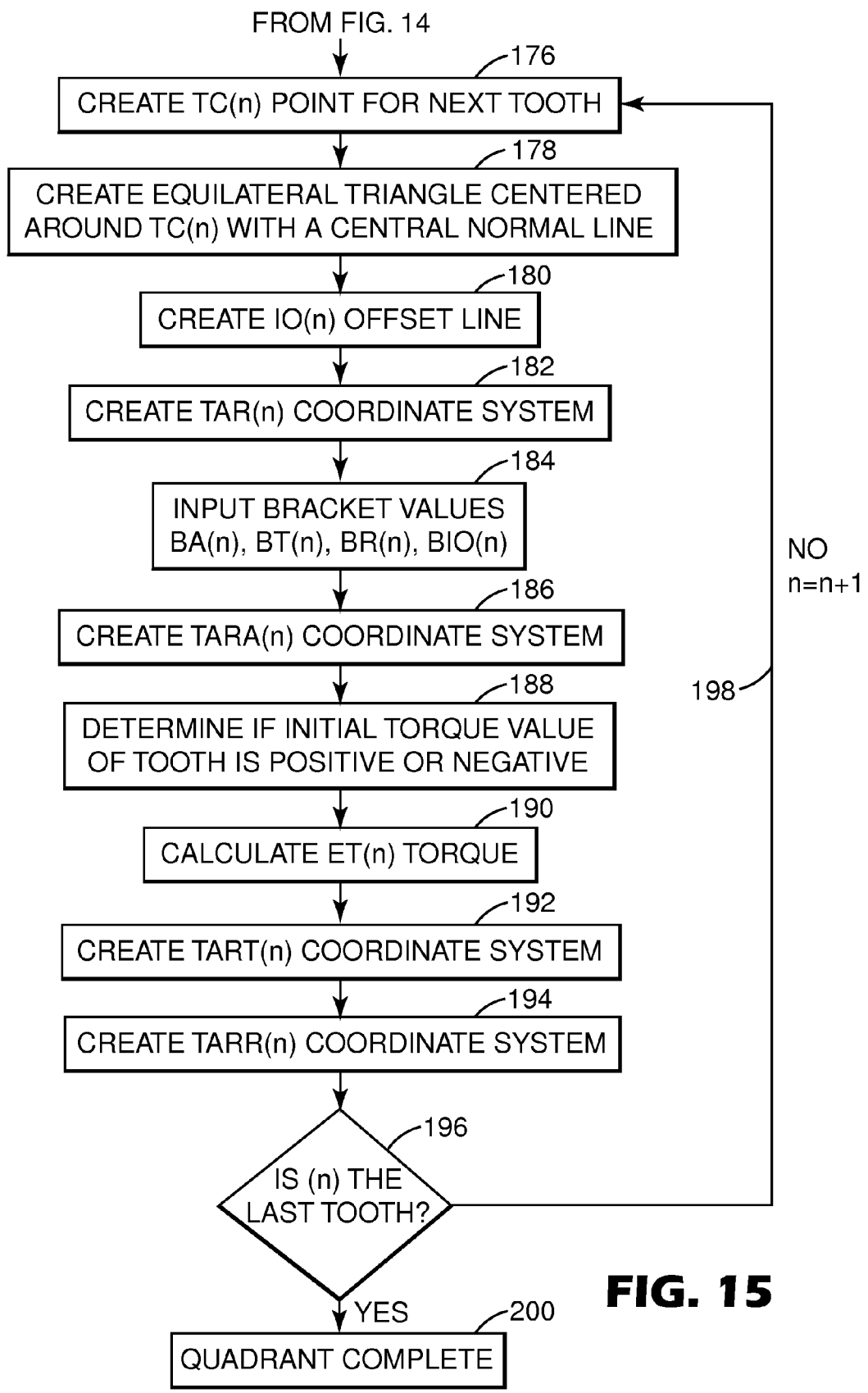
Figure 17:
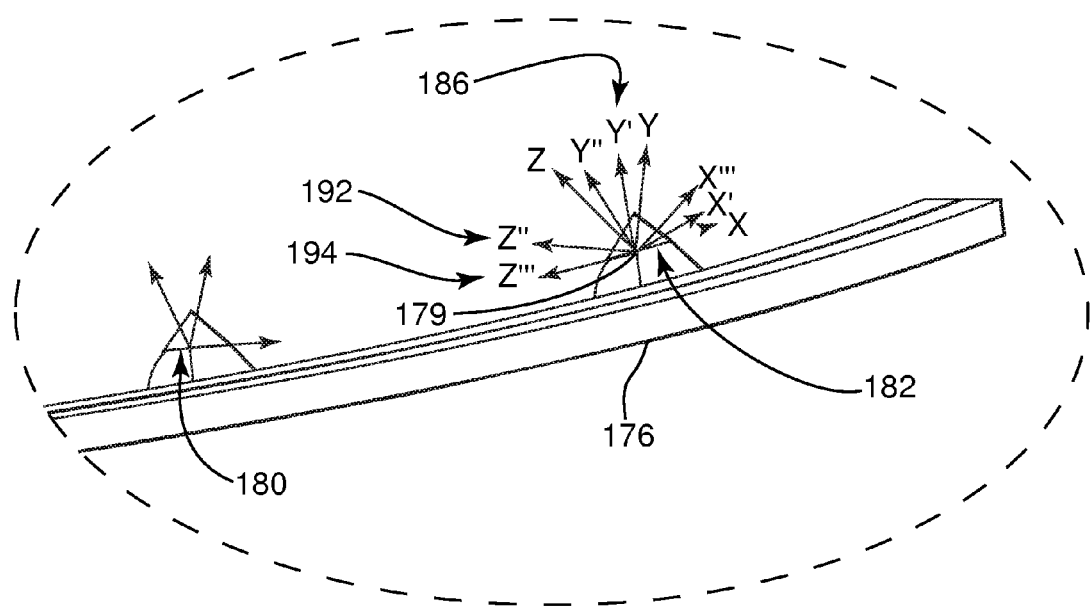
FIG. 17 is an enlarged, fragmentary view of a portion of the arch form and two of the coordinate systems illustrated in FIG. 16.

FIGS. 14-15 illustrate a flow chart of a computer program for creation of a geometric reference on an arch form. The computer program automatically creates the coordinate system, an example of which is shown in FIG. 17.

The method of creating a geometric reference on an arch form begins by selection of an arch form. The arch form may be chosen from a library of generic or common arch forms as shown by Block 150. For example, the shape of the arch form may be equivalent to the shape of the "Ortho Form" brand archwire sold by 3M Unitek Corporation. As an example, the practitioner may select a generic arch form from a library of arch forms and attempt to choose an arch form that will best move the patient's teeth to desired positions at the conclusion of treatment.

As another option, an arch form may be created by scaling an arch form as indicated by Block 152. In this option, the shape of a generic arch form is increased or decreased along one or more reference axes until reaching the shape desired by the practitioner. Scaling of the arch form may be carried out by any one of a number of methods. For example, a model of the patient's arch form may be created and measured at certain reference points, and the generic arch form can then be scaled as needed until the scaled arch form, when relaxed, is a certain, predicted shape at the conclusion of treatment. Optionally, the arch form may be scaled from a single arch form, or may be scaled from one of a number of generic arch forms that are retained in a data file containing a library of arch forms.

As another alternative, an arch form may be created by the computer with reference to electronic data representative of the patient's arch shape. For example, a hand-held camera as mentioned above may be used to scan the intra-oral cavity. The computer may then create an optimized arch form by selecting an arch form having a shape that is equal to the desired shape of the arch form at the conclusion of treatment, accommodating for the in/out dimension of the bracket.

As yet another alternative, an arch form may be provided from another source as indicated by Block 156. An example of another arch form source is a customized arch form that has been created by the practitioner.

As indicated by Block 158, data representative of the surface of the arch form, or at least approximately representative of the arch form surface, is created if it does not yet exist. The surface of the arch form could be provided by data of a solid model, wire frame data, data representing a surface or data representing a point cloud surface.

Next, and as indicated by Block 160, an AC plane, or arch center plane, is created. The AC plane extends through the center of the longitudinal axis of the arch form and the plane divides the arch form into an occlusal section and a gingival section. The AC plane could be flat. Alternatively, the AC plane could be curved such that it follows, for example, a curve of Spee or reverse curve of Spee.

As set out in Block 162, an AM plane, or arch midpoint plane, is then created. The AM plane divides the arch form into a right side and a left side. For example, the right central tooth will be on one side of the AM plane and the left central tooth will be on the opposite side of the AM plane.

Figure 16:
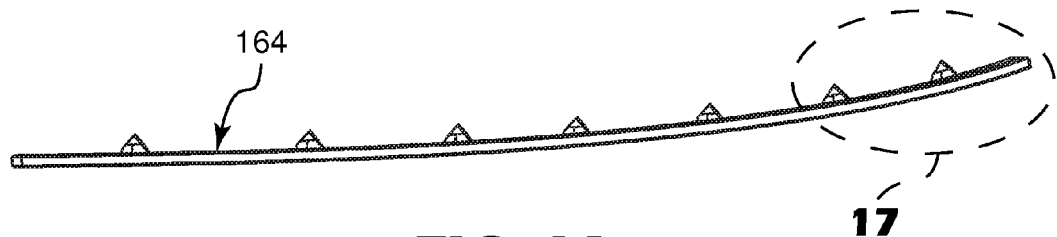
FIG. 16 is an elevational view of one quadrant of an arch form, illustrating the construction of exemplary coordinate systems along the arch form by following the method set out in blocks 14-15.

Next, and as represented by Block 164, an IAFC curve, or inner arch form curve, is created. The IAFC curve is located at the intersection of the AC plane and the lingual portion of the arch form, and is shown by the numeral 164 in FIG. 16. The IAFC curve is divided into a right side and a left side by the AM plane. The zero position of the curve is located at the intersection of the right side and the left side.

Block 166 represents the beginning of attachment of the coordinate system to a quadrant. The attachment of the coordinate system to the arch form is identical for all four quadrants. The steps that follow will set out the creation for the coordinate system for the lower right quadrant for purposes of illustration.

Figure 19:
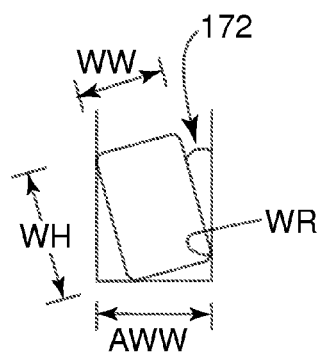
FIG. 19 is an enlarged, fragmentary, cross-sectional view of an archwire that is received in a slot of an orthodontic bracket, and illustrates, for exemplary purposes, movement of the archwire within the slot to a non-aligned position.

As shown in Block 168, the archwire dimensions are determined. The term "WW" refers to the width of the archwire in an occlusal-gingival direction. The term "WR" represents the radius of the corners of the archwire. The term "WH" represents the height of the archwire in a lingual-labial direction. FIG. 19 illustrates measurement of WW and WH.

The archwire dimensions (WW, WR and WH) may be determined by any suitable means. For example, if an arch form is selected as shown in Block 150 from a commercially available arch form, the dimensions for the arch form may be retained in memory. In instances where an arch form is created by scaling (such as set out in Block 152) or is created from scanned data (as set out in Block 154), the practitioner may elect to input the archwire dimensions to the computer based on the practitioner's past practice and expected treatment for the patient at hand.

Next, and as set out in Block 170, a dimension AWW, or archwire slot width, is determined. The AWW dimension is shown for purposes of illustration in FIG. 19. If, for example, the orthodontic appliance is selected from a library of commercially available appliances, the AWW dimension may be provided by memory storage. As another option, the practitioner may elect to input the AWW dimension into the computer according to a preferred appliance intended to be used in treatment.

As shown in Block 172, an expression angle or "EA" is then calculated. The EA is illustrated in FIG. 19 and is designated by the numeral 172. The EA is the angle between one wall of the archwire slot and one side of the archwire when the archwire is rotated to its maximum extent and is contact with the edges of the archwire slot. In instances where the archwire is fully seated in the archwire slot, the EA is equal to zero. If the archwire substantially fills the archwire slot, the EA may be zero or near zero.

Next, the width of each tooth is measured as indicated by Block 174. The tooth width is the maximum mesial-distal width of the tooth when measured normal to the BSC plane. The tooth widths are identified as TW1 up to and including TW8.

Figure 18:
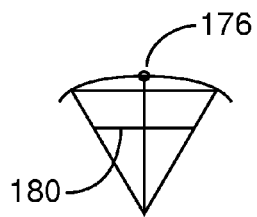
FIG. 18 is an enlarged view showing part of one of the coordinate systems depicted in FIG. 17.

The TC(n) point is then created as set out in Block 176. The TC(n) point is the location of the center of the tooth on the arch form. The TC(n) point is measured along the length of the IAFC curve, and the dimension for the location of the point is equivalent to TW(n−1)/2+TW(n)/2, where n is the number of the tooth 1 thru 8. The TC(n) point is designated by the numeral 176 in FIGS. 17 and 18. FIG. 17 is an enlargement of a portion of the arch form shown in FIG. 16.

Next, and as set out in Block 178, an equilateral triangle is created, centered around TC(n) with a center normal line. The length of the legs of the triangle represents the interaction width between the tooth and the arch form if the bracket attachment is being simulated. The width of the leg equals the mesial-distal width of the bracket slot, the points MA(n) and DB(n) are aligned to the IAFC curve, and the first leg of the triangle is from the point MA(n) to point DB(n). Point CL(n) is located at the intersection of the second and third legs of the triangle. The center line of the equilateral triangle is from point CL(n) to point TC(n), and this line is normal to the first leg of the triangle. The distance from the center line to points MA(n) and DB(n) is half of the length of the leg. The equilateral triangle centered around TC(n) and is designated by the numeral 178 in FIG. 17.

As indicated by Block 180, an IO(n) offset line is then created. The IO(n) offset line is parallel to the first leg of the equilateral triangle at a distance of IOD(n). The IO(n) offset line is indicated by the numeral 180 in FIGS. 17 and 18.

Next, and as set out in Block 182, a TAR(n) coordinate system is created. The TAR(n) coordinate system is indicated by the numeral 182 in FIG. 17. The Z axis of this coordinate system is along the equilateral triangle normal line and extends in a lingual direction. The Y axis of this coordinate system is normal to the equilateral triangle normal line and the IO(n) line. The Y axis extends in a gingival direction. The X axis is determined from the Y and Z axis following the right hand rule.

As shown in Block 184, certain aspects of the bracket prescription are then provided. These aspects include the angulation of the bracket, or "BA(n)", the torque of the bracket, or "BT(n)", the rotation of the bracket, or "BR(n)" and the in-out dimension of the bracket, or "BIO(n)". These values could be inputted by the practitioner, or alternatively retrieved from memory, and may vary for the various brackets from tooth to tooth.

Next, a TARA(n) coordinate system is created as set out in Block 186. The TARA(n) coordinate system is created by rotation of the TAR(n) coordinate system about the Z axis by the angulation angle BA(n). The Z axis is the same for both the TAR(n) coordinate system and the TARA(n) coordinate system. The TARA coordinate system is identified by the numeral 186 in FIG. 17.

The program then determines if the initial torque value of the tooth is positive or negative as described in Block 188. The width of the archwire slot is larger than the width of the archwire, and consequently the tooth may be oriented in either a positive torque value orientation or a negative torque value orientation at the beginning of treatment. If the tooth initially has a positive torque value, the value of "TS" is 1, and if the tooth initially has a negative torque value, the value of "TS" is −1. Subsequently, an "ET(n)" torque value is calculated as set out in Block 190. ET(n) is the expression torque for a tooth n, and equals the sum of the torque of the bracket (BT(n)) plus the product of the torque value (TS(n)) times the expression angle (EA).

Next, and as set out in Block 192, a TART(n) coordinate system is created. The coordinate system TART(n) and the TARA(n) coordinate system share the same X axis, but the TART(n) coordinate system is rotated by the expressed torque angle (ET(n)) about the X axis of the TARA(n) coordinate system. The TART(n) coordinate system is designated 192 in FIG. 17.

The TARR(n) coordinate system is then created as described in Block 194. The TARR(n) coordinate system and the TART(n) coordinate system share a common Y axis. However, the TARR(n) coordinate system is rotated by the rotation angle BR(n) about the Y axis of the TART(n) coordinate system. The TARR(n) coordinate system is identified by the numeral 194 in FIG. 17.

The program then determines if the value "n" represents the last tooth of the quadrant. If the answer is no, the value n is increased by 1 as described in Block 198 and the program returns to Block 176. However, if the value n represents the last tooth of the quadrant, the program recognizes that the geometric references for that quadrant have been completed as shown by Block 200.

Creation of Virtual Dentition and Occlusion

This section describes the attachment of the model teeth to the arch form as the model teeth would appear in their final positions. This section also describes the superimposition of model teeth onto one another, where the difference in orientation of the same model teeth as shown in the superimposed images is a result of the difference in effect of one prescription compared to the other. This section also describes optional methods of placing the upper and lower arch forms into occlusion with each other, and methods of automatically selecting brackets to position the teeth to desired, selected final positions.

Figure 20:
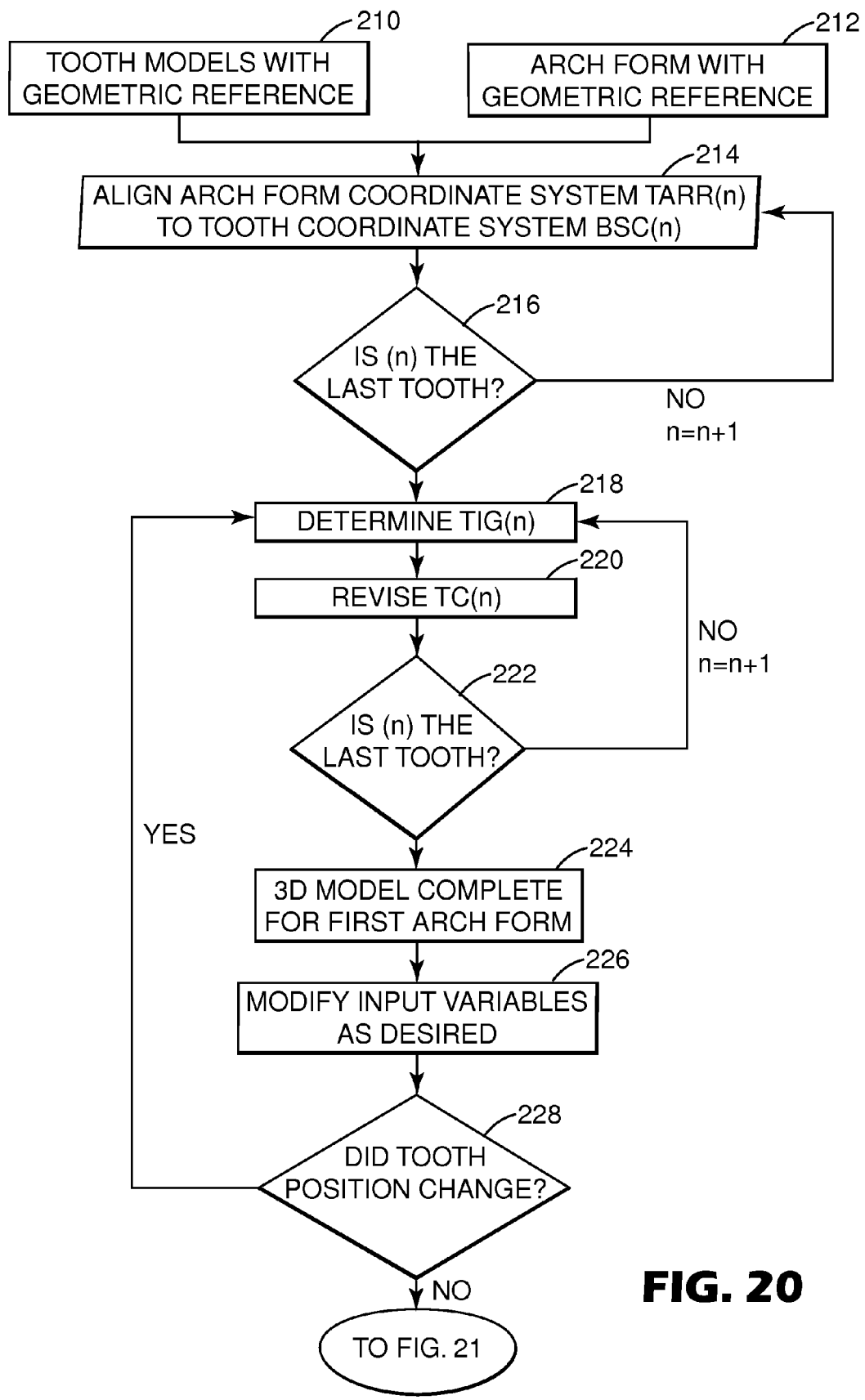
FIGS. 20-22 is a more detailed block diagram of another portion of the program illustrated in FIG. 1, showing an example of a method of creating virtual dentition and occlusion.
Figure 21:
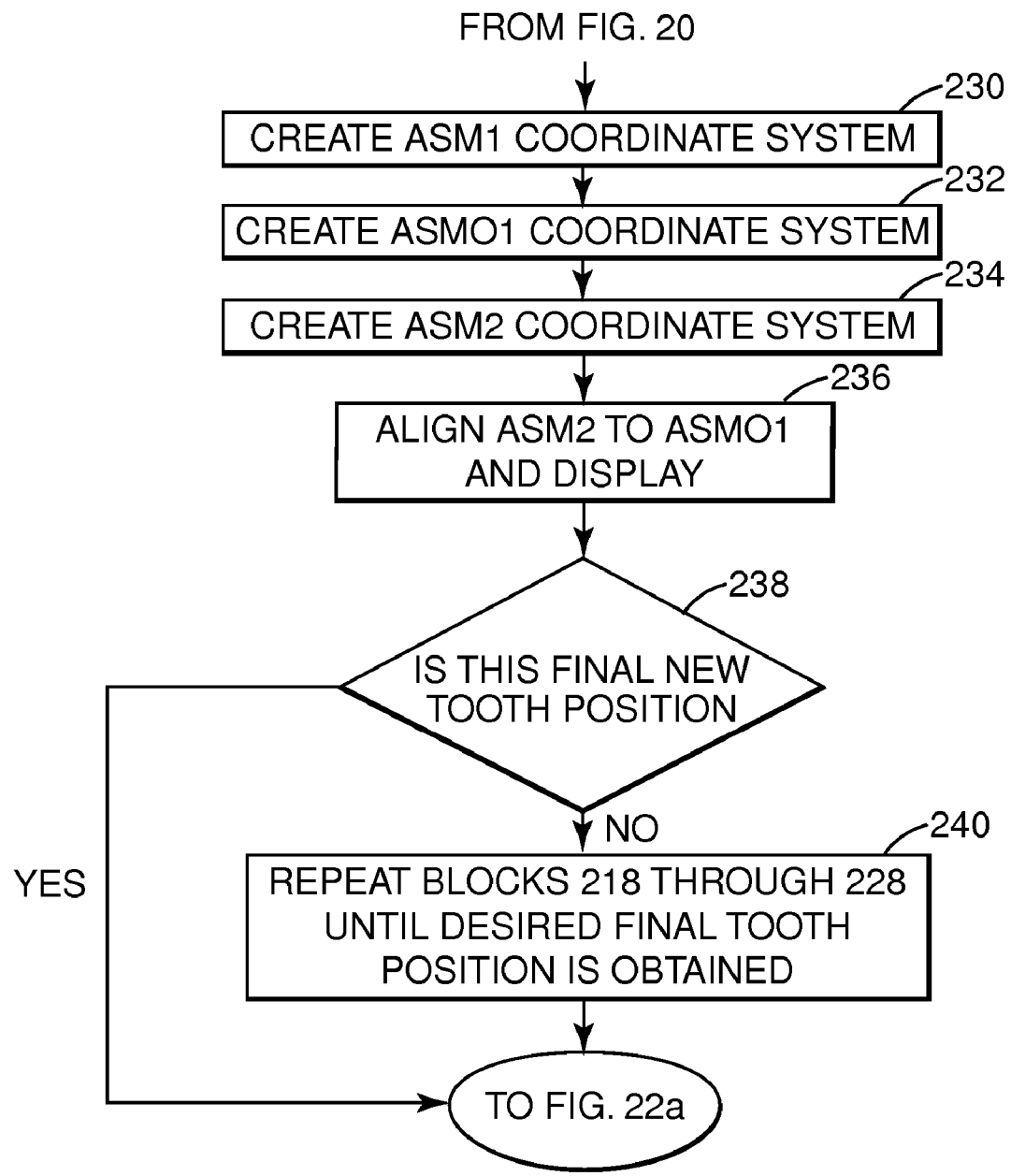
Figure 22A:
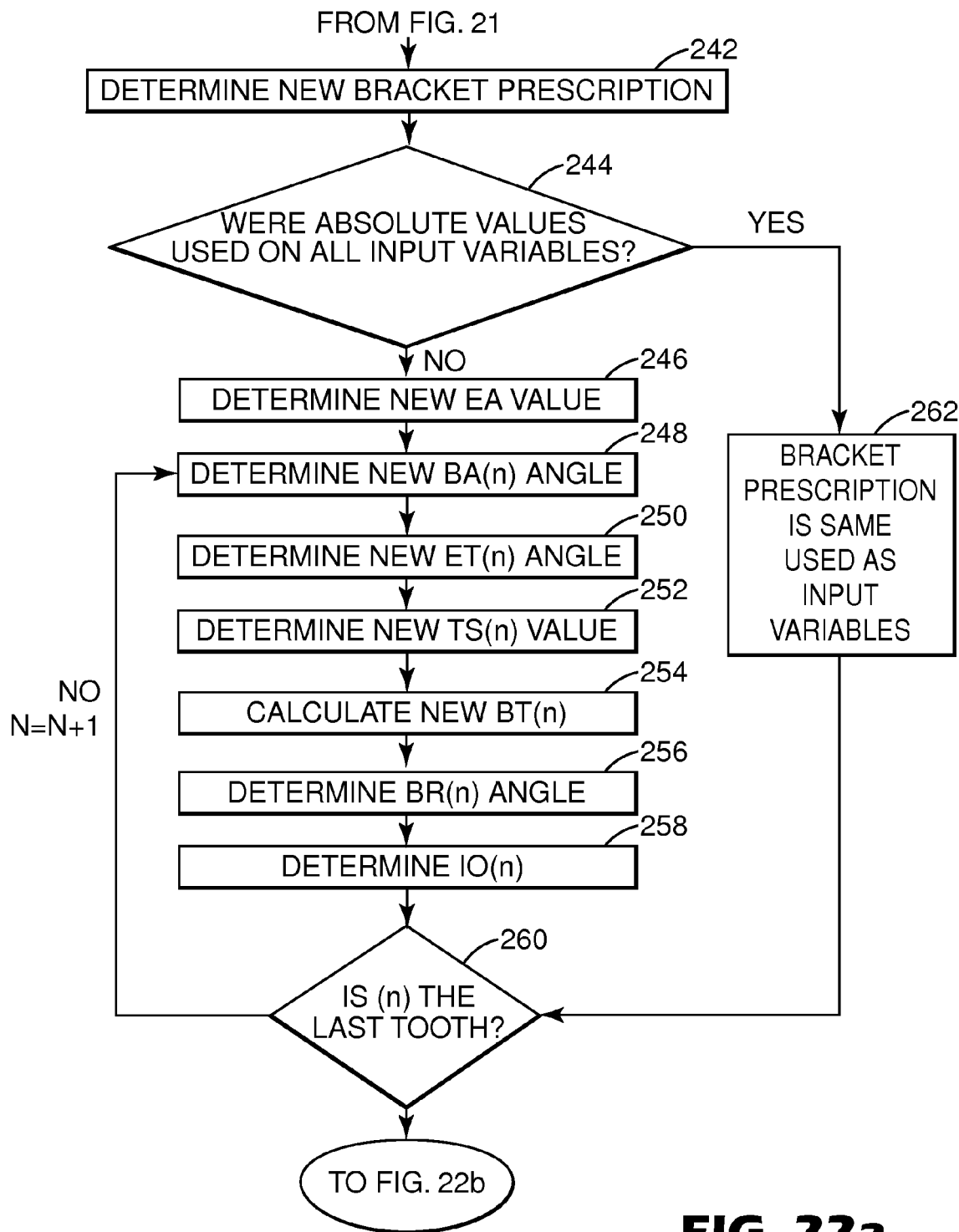
Figure 22B:
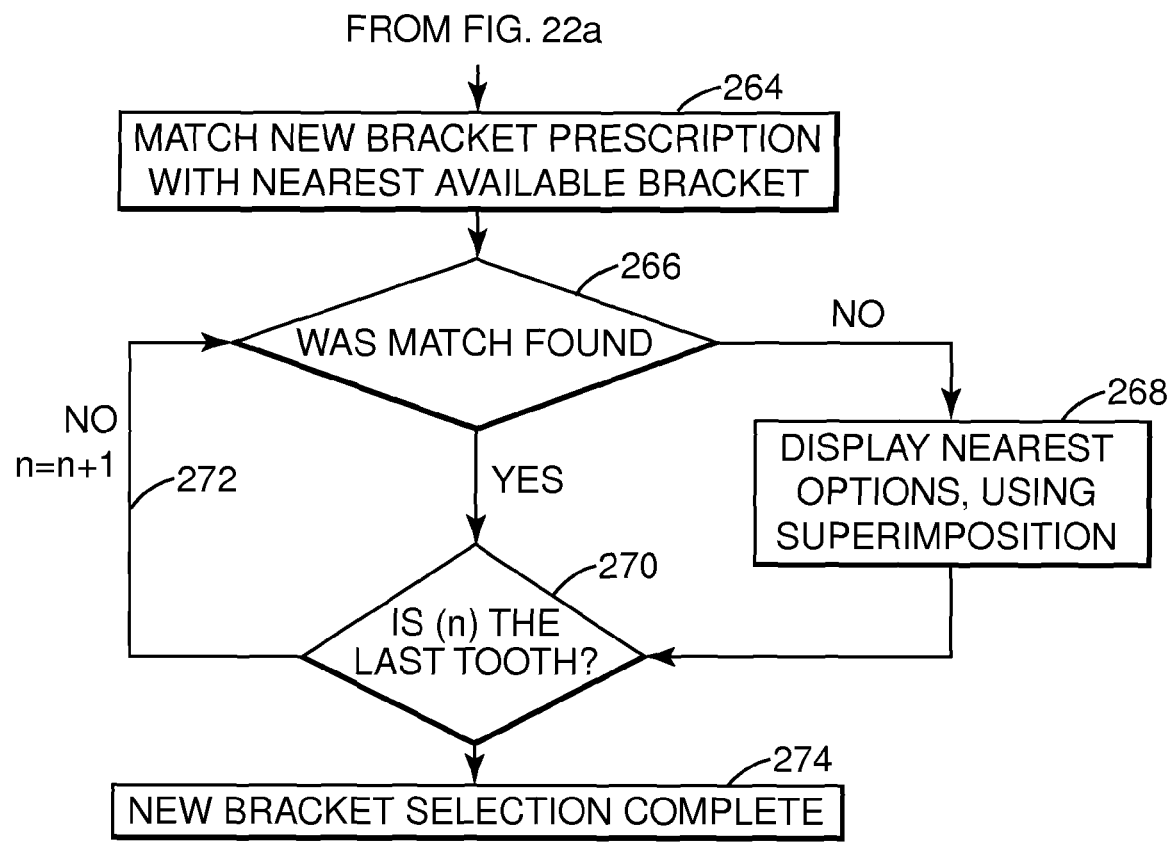

The resulting models in superimposed display provide a powerful analytical technique for reviewing the effects of different prescriptions as an aid for better understanding the resulting, final orientations of the teeth at the conclusion of treatment. As a consequence, the program facilitates selection of the correct bracket and/or archwire for positioning the teeth to desired positions. FIG. 20-22 illustrate flow charts of a computer program for creation of virtual dentition and occlusion. The program automatically positions the model teeth along the desired arch form.

Referring initially to FIG. 20, this section of the program begins with the tooth models having a geometric reference as described in Block 210 which was previously obtained by the program upon reaching Block 140 described above. This section also begins with use of the arch form having a geometric reference as described in Block 212, which was previously obtained when the program reached Block 200 as described above.

Figure 23:
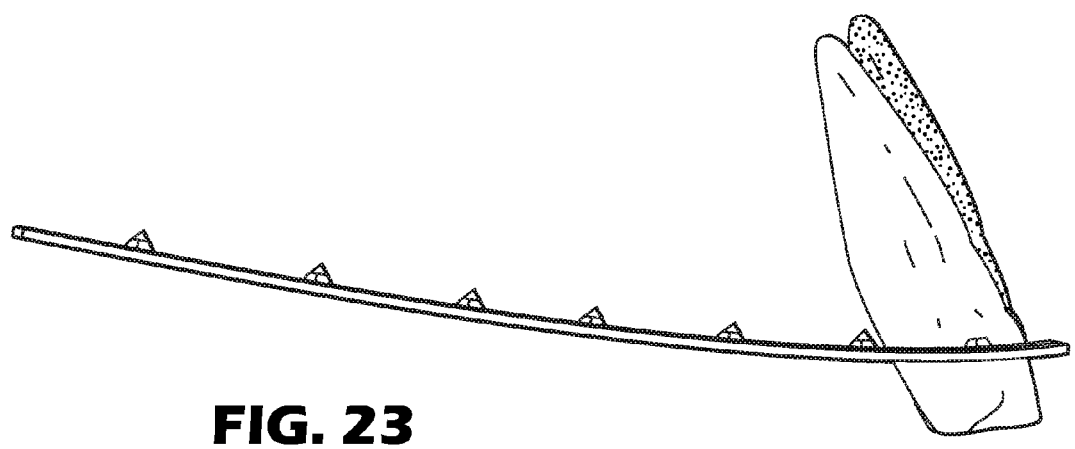
FIG. 23 is a perspective view of an arch form and a single model tooth, illustrating an example of use of the coordinate systems to attach the model tooth to the arch form in a certain orientation.

Next, and as set out in Block 214, the arch form coordinate system TARR(n) is aligned to the tooth coordinate system BSC(n). This part of the program assembles the tooth models to the arch form in an orientation resulting from the initially selected prescription. The alignment of TARR(n) to BSC(n) is identified by the numeral 214 in FIG. 23.

Next, the program determines whether or not n is the last tooth in the arch. If the answer is no, the value of n is increased by 1 and the program returns to Block 214. If the answer is yes, the program proceeds to Block 218.

In Block 218, an interference value, or "TIG(n)" is obtained. If the value of TIG(n) is positive, this indicates that there is an interference between the teeth (i.e., the virtual teeth overlap each other). If the value of TIG(n) is negative, this indicates that there is a gap between the virtual teeth.

The TC(n) tooth point dimension is then corrected, as indicated by Block 220. The value of TIG(n) is added to the value of TC(n) to obtain a new value for TC(n).

The program then proceeds to Block 222, where the program determines whether or not n is the last tooth. If the answer is negative, the value of n is increased by 1 and the program returns to Block 218. If the answer is positive, the program proceeds to Block 224.

Once the program has reached Block 224, the 3D model has been completed for the first prescription. At this point, the 3D model may optionally be displayed so that the practitioner can view the various orientations of the model teeth along the dental arch. The positions of the model teeth are reached as a result of the prescription of the brackets and archwire. For example, the position of the model teeth represent final positions attained for brackets having a certain angulation, torque, rotation, in-out dimension, bracket width, bracket position on tooth surface (both in mesial-distal directions and in occlusal-gingival directions), archwire size, archwire slot size, and tooth starting positions, all of which can be provided to the program as input variables.

As a result of the practitioner's review of the resulting positions of the model teeth as described in Block 224, the practitioner may elect to modify one or more of the input variables. The modification of the input variables is described in Block 226. The input variables can be modified in an incremental fashion by changing one or more of the variables in a step-wise manner. As another option, the input variables can be changed to correspond to known prescription values, such as values commonly used for brackets that are constructed according to the known techniques. Examples of well-known techniques include those taught by Drs. McLaughlin, Bennett and Trevisi (the "MBT" brand bracket prescription), those taught by Dr. Ron Roth and those taught by Dr. Lawrence F. Andrews. As still another option, the input variables can be modified in a manner selected by the practitioner to achieve certain results.

If the modification of the input variables as set out in Block 226 changes the position of the tooth, the program proceeds from Block 228 to Block 218 for a repetition of the steps described above. If the tooth position has not changed when the program reaches Block 228, the program proceeds to Block 230 as shown in FIG. 21.

Figure 24:
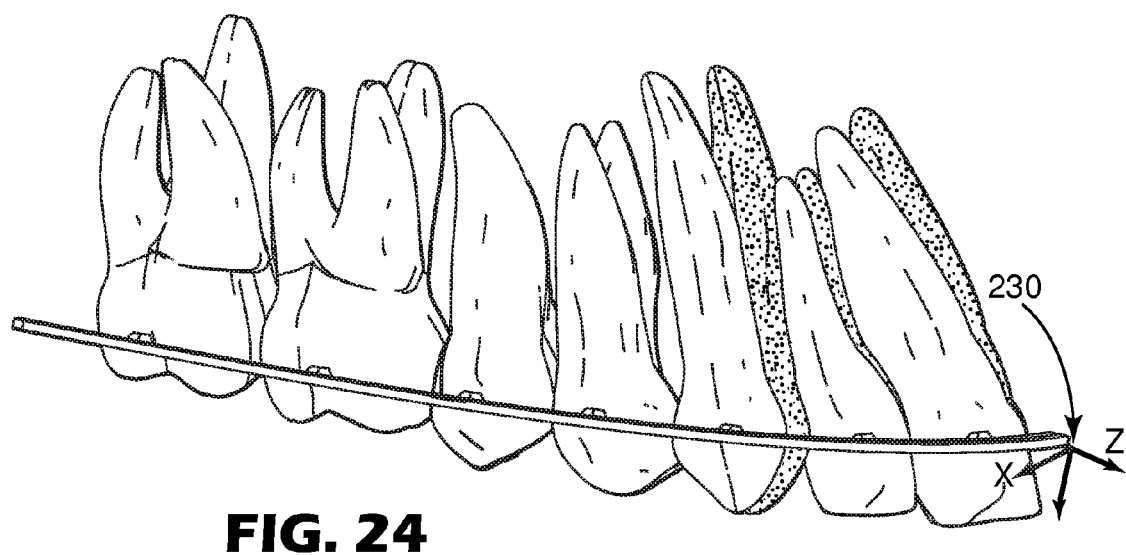
FIG. 24 is a view somewhat similar to FIG. 23 except that all of the model teeth in the quadrant have been assembled to the arch form.

The program flow chart set out in FIG. 21 describes an example of one method of superimposing images of model teeth, where the difference in the superimposed images is a result of different prescriptions. As shown in Block 230, the ASM1 coordinate system is created on the first arch form. The ASM1 coordinate system is located at the zero position of the IAFC1 arch form curve. The X axis of the ASM1 coordinate system is parallel to the AC1 arch form plane and normal to the AM1 arch form plane and extends in a direction toward the right. The Y axis of the ASM1 coordinate system is parallel to the AM1 arch form plane and normal to the AC1 arch form plane, and points in a gingival direction. The Z axis of the ASM1 coordinate system is derived by following the right hand rule. The ASM1 coordinate system is designated 230 in FIG. 24.

Next, and as set out in Block 232, the ASMO1 coordinate system is created. The ASMO1 coordinate system is offset from the ASM1 coordinate system. The amount of the offset is arbitrary. As a default, for example, the occlusal tips or the ends of the roots of the lower anterior teeth or cuspid teeth could be aligned.

The ASM2 coordinate system is then created on the second arch form as indicated in Block 234. The ASM2 coordinate system is located at the zero position of the IAFC2 arch form curve. The X axis of the ASM2 coordinate system is parallel to the AC2 arch form plane, is normal to the AM2 arch form plane and points to the right. The Y axis of the ASM2 coordinate system is parallel to the AM2 arch form plane, is normal to the AC2 arch form plane and points in the gingival direction. The Z axis of the ASM2 coordinate system is derived by following the right hand rule.

Next, and as described in Block 236, the coordinate system ASM2 is aligned to the coordinate system ASMO1. At this point, the resulting models are superimposed, and the differences in the tooth positions as a result of different prescriptions on the same teeth are readily apparent.

Next, the program proceeds to Block 238, where the computer determines whether or not a final new tooth position has been reached. If the answer is positive, the program proceeds to Block 242 as set out in FIG. 22. If the answer is negative, the program proceeds to Block 240. In Block 240, the steps set out in Blocks 218 through Blocks 228 are repeated until the final tooth position is attained. The program then proceeds to Block 242.

The flow chart set out in FIG. 22 describes a method for computer selection of a bracket prescription, if needed, as a result of the practitioner's review of the displayed images of the tooth models described above. To determine the new bracket prescription, the program proceeds to Block 244 and determines whether or not absolute values were used on each of the input variables, such as the input variables mentioned in Block 226. If the answer to this question is positive, the bracket prescription includes the same values used for the input variables as shown by Block 262. If the answer is negative, the program proceeds to Block 246.

In Block 246, a new EA value is determined. Next, the program proceeds to Block 248, where a new BA(n) angle is determined to obtain a bracket angulation value. The program then proceeds to Block 250 where the ET(n) angle is determined. The ET(n) angle represents a new expressed torque value for the bracket.

The program then proceeds to Block 252, where a new TS(n) value is determined. The TS(n) value represents the tooth start position for the new bracket prescription.

Next, the program proceeds to Block 254, where a new BT(n) value, or bracket torque angle, is determined. The BT(n) value is equal to the ET(n) value minus the product of the TS(n) value times the new EA value.

The program then proceeds to Block 256, where the BR(n) angle is determined. The BR(n) angle represents the new bracket rotation angle.

Subsequently, the program proceeds to Block 258, where a new IO(n) value is determined. The IO(n) value represents the in-out dimension of the new bracket in the new position.

The program then proceeds to Block 260, where the value of n is evaluated. If n represents a value that is not the value for the last tooth, the value of n is increased by 1 and the program returns to Block 248. If the value for n is equal to the value for the last tooth, the program proceeds to Block 264.

In Block 264, the program compares the new bracket prescription with the prescription of various brackets available. Available brackets could include, for example, brackets that are available in the practitioner's inventory, in the manufacturer's inventory, or that can be constructed by the manufacturer when desired.

Next, the program proceeds to Block 266. If a match was not found in Block 264, the program proceeds to Block 268, where the result obtained by the nearest available bracket or brackets are displayed in superimposed relation to the results attained at the conclusion of the method set out in Block 260. The superimposition of images as described in Block 268 is a benefit to the practitioner, because the practitioner can readily observe and compare the results obtained with the preferred bracket prescription and the nearest available bracket prescription. The superimposed images help the practitioner to decide whether or not the nearest available bracket prescription is satisfactory for the treatment at hand.

The program then proceed to Block 270, where the program determines whether or not n is a value equivalent to the value for the last tooth. If the answer is negative, the value for n is increased by 1 as set out in Block 272 and the program return to Block 266. If the answer is positive, the program proceeds to Block 274, which indicates that the selection method of the brackets is complete. Moreover, if the program upon reaching Block 266 determines that a match was found, the program proceeds directly to Block 270 and follows the steps described above.

The display of the superimposed images as set out in Block 268 can also optionally include other information as well. For example, the display can include numerical information pertaining to the bracket prescriptions. Values such as bracket torque, angulation and slot width can be displayed, optionally in tabular format. In this manner, the differences of the two bracket prescriptions under comparison can be readily quantified.

Preferably, the superimposed images appear in contrast so that the relative effect of the first brace and the second brace can be observed. For example, the image of the first brace may appear in a first color, and the image of the second brace may appear in a second color that contrasts with the first color. As such, the difference in position of the roots, crowns or other features of each tooth can be easily determined.

Other options for image contrast are also possible. For example, the shading of the images may be different from one another such as the use of different types of cross-hatching. As another option, the texture of the images may appear different, such as a stippled image next to a smooth-appearing image. As another example, the shape of the perimeter of the images may vary, such that one image has a perimeter with bold lines, while the other image has a perimeter with dashed or dotted lines. Other types of image contrast are also possible.

The concepts set out above may also be used with a single group of appliances so that the practitioner can visually determine the positions of the teeth with the appliances during a certain, selected stage of orthodontic treatment and compare those results with the positions of the teeth during a preceding stage of orthodontic treatment. The preceding stage may be an initial position of the teeth as they appear before treatment begins. As another option, the images of the teeth in the preceding stage may represent an intermediate stage of treatment, such as a point in time at the conclusion of one archwire before the second, third, etc. or final archwire is installed. In orthodontic treatment, it is common to use archwires having differing characteristics at selected intervals of time, and the teeth may not be moved to the final or finished positions until such time as the last archwire is in place and the teeth have moved in response to that last archwire.

The invention as described above is particularly useful for enabling the orthodontist to select a preferred brace or preferred components of a brace from a list of available braces or components of a brace, such as a catalog list from a manufacturer. Alternatively, however, the invention may also advantageously be used to manufacture custom-made brace components. In that instance, the methods set out above may be used by initially selecting a prescription from an initial estimate of a suitable prescription, and by then using the steps set out above to observe the expected results. If needed, the prescription can be modified as many times as necessary until the desired results are achieved. A programmed milling machine or other automated manufacturing device may then be used to custom-make the selected components. Such a method could be used, for example, to custom make brackets or custom-bend archwires. When used in lingual treatment, the components can be selected to provide a very low profile so that patient comfort is increased.

A variety of other alternatives are also possible. Accordingly, the invention should not be deemed limited to the specific, presently preferred embodiments set out above, but instead only by a fair scope of the claims that follow along with their equivalents.

What is claimed is:

1. A method of selecting orthodontic brackets for an orthodontic brace comprising:
   providing digital tooth data representative of a number of teeth of a dental arch;
   receiving input from a practitioner specifying data for a prescription for a set brackets of an orthodontic brace for at least some of the teeth in the dental arch;
   executing a computer program that determines resulting positions of the teeth as they might appear when the brace is mounted on corresponding teeth using at least in part the digital tooth data and the data relating to the prescription;
   providing a library of available brackets including prescription data in memory relating to at least one aspect of each bracket;
   after determining the resulting positions of the teeth, executing the computer program to compare the prescription data specified by the practitioner for the set of brackets of the brace with the prescription data of the available brackets in the library; and
   executing the computer program to select the brackets in the library that have prescription data that best matches the prescription data of the set of brackets of the orthodontic brace.

2. The method of selecting orthodontic brackets for an orthodontic brace according to claim 1 wherein the library of available brackets is selected from a list of available brackets in the practitioner's inventory or in the manufacturer's inventory.

3. The method of selecting orthodontic brackets for an orthodontic brace according to claim 1 and including the act of displaying the determined positions of the teeth.

4. The method of selecting orthodontic brackets for an orthodontic brace according to claim 1 and including the act of displaying the selected brackets.

5. The method of selecting orthodontic brackets for an orthodontic brace according to claim 1 and including the acts of:
   selecting a second orthodontic brace for at least some of the same teeth in the dental arch, wherein the second brace includes a second set of brackets having a certain prescription, and wherein at least one bracket of the second brace has a prescription that is different than the prescription of the corresponding bracket of the other brace; and
   determining second positions of the teeth as they might appear when the second brace is mounted on corresponding teeth using at least in part the digital tooth data and data relating to the prescription.

6. The method of selecting orthodontic brackets for an orthodontic brace according to claim 1 and including the act of generating with a computer a purchase order that uses at least in part the prescription data of the selected brackets.

7. The method of selecting orthodontic brackets for an orthodontic brace according to claim 1 wherein the act of providing a set of data representative of a number of teeth includes the act of providing data that represents a surface of the patient's teeth.

8. The method of selecting orthodontic brackets for an orthodontic brace according to claim 1 and including the act of storing in memory an identification of the selected brackets.

9. The method of selecting orthodontic brackets for an orthodontic brace according to claim 1 and including the act of comparing a preferred orthodontic bracket to a nearest available orthodontic bracket using the computer.

10. The method of selecting orthodontic brackets for an orthodontic brace according to claim 1 wherein the prescription data specified by the practitioner includes data relating to one or more of the following: the angulation of the bracket, the torque of the bracket, the rotation of the bracket, the in-out dimension of the bracket, the depth of an archwire slot of the bracket, the arch of an archwire slot of the bracket, the length of the archwire slot of the bracket, the material of the bracket, and the material of an archwire slot liner of the bracket.

11. The method of selecting orthodontic brackets for an orthodontic brace according to claim 1 and including displaying prescription data of the selected brackets.

12. The method of selecting orthodontic brackets for an orthodontic brace according to claim 1 wherein the act of displaying prescription data includes displaying prescription data in tabular format.

13. The method of selecting orthodontic brackets for an orthodontic brace according to claim 1 comprising:
   determining second resulting positions of the teeth as they might appear when the brace is mounted on corresponding teeth using the brackets selected from the library by the computer to have prescription data that best matches the prescription data specified by the practitioner for the set of brackets of the brace; and
   displaying the resulting positions of the teeth achieved by the brace having prescription data specified by the practitioner and the second resulting positions of the teeth in superimposition to aid the practitioner in determining whether the brackets selected from the library by the computer are satisfactory.

* * * * *

UNITED STATES PATENT AND TRADEMARK OFFICE
CERTIFICATE OF CORRECTION

| | |
|---|---|
| PATENT NO. | : 7,766,653 B2 |
| APPLICATION NO. | : 11/555415 |
| DATED | : August 3, 2010 |
| INVENTOR(S) | : Robert C. Manemann et al. |

It is certified that error appears in the above-identified patent and that said Letters Patent is hereby corrected as shown below:

Column 1
Lines 10-11, Delete "currently pending." and insert -- now abandoned. --, therefor.

Lines 27-28, In Claim 9, after "including" delete "the act of".
Line 43, In Claim 12, after "wherein" delete "the act of".

Signed and Sealed this

Twenty-sixth Day of October, 2010

David J. Kappos
*Director of the United States Patent and Trademark Office*